(12) United States Patent
Attardo et al.

(10) Patent No.: US 10,301,308 B2
(45) Date of Patent: May 28, 2019

(54) AZETIDINE DERIVATIVES FOR TAU IMAGING

(71) Applicant: Eli Lilly and Company, Indianapolis, IN (US)

(72) Inventors: Giorgio Attardo, Bryn Mawr, PA (US); Carey Lynn Horchler, Wayne, PA (US); Shyamali Ghosh, Norristown, PA (US); Hui Xiong, Chesterbrook, PA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/763,608

(22) PCT Filed: Nov. 4, 2016

(86) PCT No.: PCT/US2016/060621
§ 371 (c)(1),
(2) Date: Mar. 27, 2018

(87) PCT Pub. No.: WO2017/083198
PCT Pub. Date: May 18, 2017

(65) Prior Publication Data
US 2018/0282322 A1    Oct. 4, 2018

Related U.S. Application Data

(60) Provisional application No. 62/254,906, filed on Nov. 13, 2015.

(51) Int. Cl.
| | |
|---|---|
| *A61K 51/00* | (2006.01) |
| *A61M 36/14* | (2006.01) |
| *C07D 471/04* | (2006.01) |
| *A61K 51/04* | (2006.01) |
| *C07B 59/00* | (2006.01) |

(52) U.S. Cl.
CPC ........ *C07D 471/04* (2013.01); *A61K 51/0444* (2013.01); *A61K 51/0453* (2013.01); *A61K 51/0455* (2013.01); *C07B 59/002* (2013.01); *C07B 2200/05* (2013.01)

(58) Field of Classification Search
CPC .................. C07B 59/002; C07B 2200/05
USPC ....................................... 424/1.89
See application file for complete search history.

(56) References Cited

U.S. PATENT DOCUMENTS

| | | | |
|---|---|---|---|
| 2005/0009865 A1* | 1/2005 | Kudo | A61K 31/47 514/311 |
| 2010/0172836 A1* | 7/2010 | Benedum | A61K 51/0455 424/1.89 |
| 2011/0182812 A1 | 7/2011 | Szardenings et al. | |

OTHER PUBLICATIONS

Manna, et al., "Metal-Free Annulation of Arenes with 2-Aminopyridine Derivatives: The Methyl Group as a Traceless Non-Chelating Directing Group," Angewandte Chemie International Edition, Jun. 18, 2014, vol. 53, No. 31, pp. 8163-8166.
Examination Report No. 1 for Australian Patent Application No. 2016351609 (dated Sep. 13, 2018).

* cited by examiner

*Primary Examiner* — Michael G. Hartley
*Assistant Examiner* — Sean R Donohue
(74) *Attorney, Agent, or Firm* — Kyle W. Grimshaw

(57) ABSTRACT

The present invention provides a novel compound of the formula: methods of making this compound, methods of using this compound for tau imaging, and preparations of tau imaging formulations.

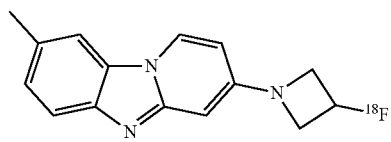

9 Claims, 10 Drawing Sheets

AZETIDINE DERIVATIVES FOR TAU IMAGING

The present invention relates to a novel compound 3-(3-fluoroazetidin-1-yl)-8-methylbenzo[4,5]imidazo[1,2-a]pyridine, and the $^{18}$F labelled version 3-(3-[18F]-fluoroazetidin-1-yl)-8-methylbenzo[4,5]imidazol[1,2-a]pyridine, and to intermediates for preparation of these compounds, and to methods of using these compounds for tau imaging, and to compositions and formulations of these compounds for diagnostic imaging, and to methods of imaging using these compounds, compositions, and formulations.

Alzheimer's disease (AD), a leading cause of dementia, develops in one percent of the population between the ages 65 and 69, and increases to 40-50% in those 95 years and older. AD patients exhibit telltale clinical symptoms that include cognitive impairment and deficits in memory function. In these patients, the presence of AD is confirmed by heavy senile plaque burden and neurofibrillary tangles (NFT) found in the cerebral cortex upon post mortem histopathological examination. The mature senile plaques consist of extracellular β-amyloid peptides derived from enzymatic processing of amyloid precursor protein and intracellular neurofibrillary tangles (NFT), which are derived from filaments of hyperphosphorylated tau proteins. Aggregates of hyperphosphorylated tau, such as neurofibrillary tangles, are linked to the degree of cognitive impairment in Alzheimer's disease. In AD and various other tauopathies, tau aggregates appear in particular brain regions and patterns that are linked to disease risk, onset, and or progression, and these regions and patterns are known to skilled artisans. In AD patients, tau-containing tangles first appear in brain regions that are very closely linked to memory, and pathologic studies show that tangles may correlate even more strongly with cognition than plaques. Signals arising from a tau imaging agent in these regions and patterns can be used by skilled artisans to better monitor and diagnose the risk, onset and progression of the particular disease state. (See *Correlation of Alzheimer disease neuropathologic changes with cognitive status: a review of the literature*. Nelson P T et al., *J Neuropathol Exp Neurol*. 2012 May; 71(5):362-81.) Thus, simple noninvasive methods, for detecting and/or quantitation of tau deposits in patients are eagerly sought. (See M. Maruyama et al., "*Imaging of tau pathology in a tauopathy mouse model and in Alzheimer patients compared to normal controls*". Neuron. 79: 1094-1108, 2013. C. Mathis and W. Klunk. "*Imaging Tau Deposits In Vivo: Progress in Viewing More of The Proteopathy Picture*", Neuron. 79: 1035-10-37, 2013).

Existing agents for PET imaging of tau are known in the art, for example such agents are recited in WO2009/102498, and a compound recently in clinical evaluation, [$^{18}$F]T807 (also known as AV-1451), is recited in WO 2013/176698. (See also [(18)*F*]*T807. a novel tau positron emission tomography imaging agent for Alzheimer's disease*. Xia C F, et al., *Alzheimer's Dement*. 2013 November; 9(6):666-76.)

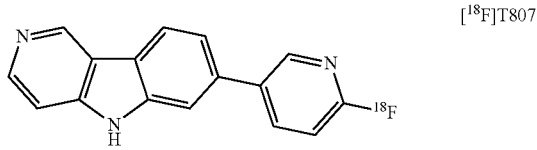 [SMILES: [18F]c1ccc(-c2ccc3c(c2)[nH]c2ccncc23)cn1]

[$^{18}$F]T807

However, existing tau imaging compounds have technical attributes that could be improved by the design of innovative agents which may provide enhanced tau images, with improved tau signaling and minimal non-tau signaling.

Thus, improved methods for detecting and/or quantitation of tau in patients are eagerly sought.

There are several potential benefits of imaging tau in the brain with improved imaging agents. Enhanced tau imaging will improve diagnosis by identifying potential patients, those having high levels of tau in the brain, who may have increased chance of developing AD. Imaging with an improved PET agent will also be useful to monitor tau accumulation and localization, and or progression of AD and or other tauopathies, and when anti-tau drug treatments become available, tau imaging may provide an essential tool for monitoring treatment.

The present invention provides novel compounds, compositions, formulations and methods for tau imaging. Improved technology advancing the capacity to image tau in patients is thus also needed to expand the clinical benefits and impact of diagnostic tau imaging. An improved imaging agent will provide enhanced tau images, as compared with known agents, producing images with better clarity due to strong tau signals and decreased non-tau signals.

The present invention provides the compound 3-(3-[18F]-fluoroazetidin-1-yl)-8-methylbenzo[4,5]imidazo[1,2-a]pyridine, also referred to herein as "Compound 8", which can be structurally represented as the compound of formula I:

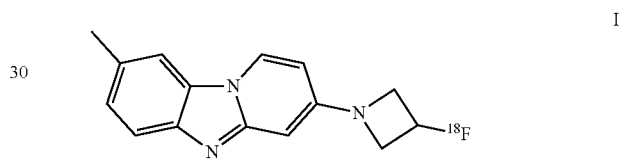

I

The present invention also provides the compound 3-(3-fluoroazetidin-1-yl)-8-methylbenzo[4,5]imidazo[1,2-a]pyridine, also referred to herein as "Compound 4", which can be structurally represented as the compound of formula II:

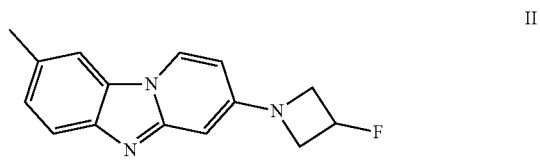 [SMILES: Cc1ccc2nc3cc(N4CC(F)C4)ccn3c2c1]

II

The present invention further provides the use of the compound of formula I and/or the compound of formula II, and/or mixtures thereof, for the preparation of tau imaging agents, and tau PET imaging.

The present invention further provides intermediates for preparation of the compound of formula I or the compound of formula II. The present invention provides a compound of formula II (indicated as Compound 8 below) prepared from a compound of formula 7:

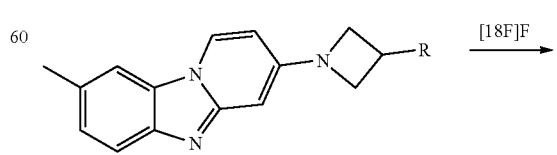

7

-continued

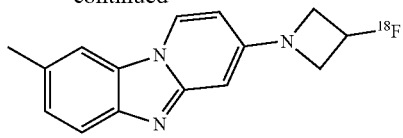

8

The invention further provides a compound of formula I prepared from a compound of formula Ia or formula Ib. A preferred species of the present invention is a compound of formula Ia.

Ia

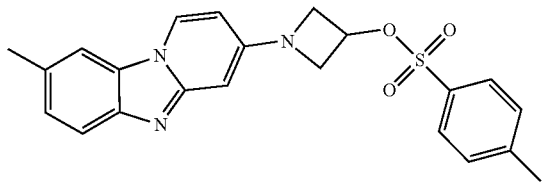

Another preferred species of the present invention is a compound of formula Ib:

Ib

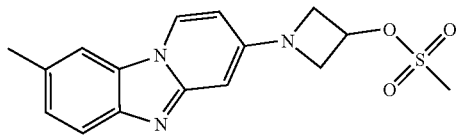

The present invention provides the use of compounds of formula I, Ia, Ib or II, for the manufacture of a radiopharmaceutical agent for imaging tau in humans. In another aspect the invention provides methods of preparing compounds of formula I, Ia, Ib or II. In another aspect the invention provides methods of preparing Compound 8 from compounds of formula Ia, or Ib. Particularly preferred is the method of preparing Compound 8, or pharmaceutically acceptable salt thereof, from the compound of formula Ia. In another aspect the invention provides a pharmaceutical composition comprising Compound 8, or pharmaceutically acceptable salt thereof, and a pharmaceutically acceptable diluent or carrier. In another aspect the invention provides a pharmaceutical composition comprising Compound 8, or pharmaceutically acceptable salt thereof, and Compound 4, or pharmaceutically acceptable salt thereof, and a pharmaceutically acceptable diluent or carrier. In another aspect the invention provides a pharmaceutical composition comprising Compound 8, or pharmaceutically acceptable salt thereof, which is formulated in 10% EtOH (v/v), 0.45% (w/v) sodium ascorbate in 0.9% sodium chloride, preferably for use in humans. In another aspect the invention provides a pharmaceutical composition comprising Compound 8, or pharmaceutically acceptable salt thereof, prepared from a compound of formula Ia or Ib, which is formulated in 10% EtOH (v/v), 0.45% (w/v) sodium ascorbate in 0.9% sodium chloride, preferably for use in humans. The present invention also provides methods of imaging tau comprising introducing into a patient a detectable quantity of Compound 8, or pharmaceutically acceptable salt thereof, or a composition thereof, preferably prepared from a compound of a compound of formula Ia or Ib.

The present invention provides a process of making a compound of the formula I:

I

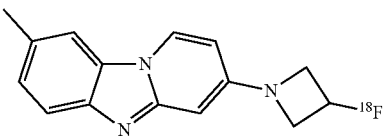

comprising reacting 1-(8-methylbenzo[4,5]imidazo[1,2-a]pyridin-3-yl)azetidin-3-yl 4-methylbenzenesulfonate, represented by the formula:

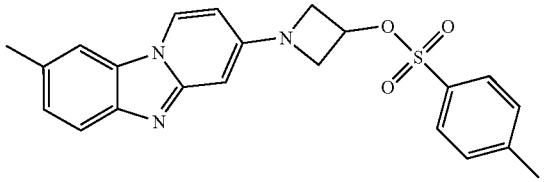

with a source of [$^{18}$F]fluoride.

The present invention provides a process of making a compound of the formula I:

I

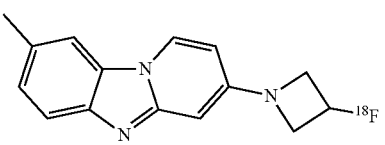

comprising reacting a compound of formula Ib:

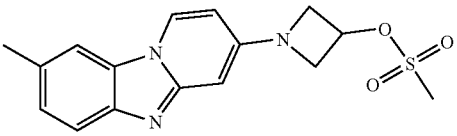 [SMILES: Cc1ccc2nc3cc(N4CC(OS(C)(=O)=O)C4)ccn3c2c1]

with a source of [18F]fluoride.

The present invention provides a method of imaging tau comprising: introducing into a mammal a detectable quantity of the compound:

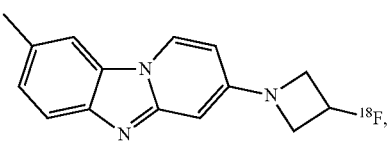

allowing sufficient time for said compound to become associated with tau, and detecting said compound.

The following Schemes, Preparations, and Examples are provided to better elucidate the practice of the present invention. Suitable reaction conditions for the steps of these Schemes, Preparations, and Examples are well known in the art and appropriate modification of reaction conditions, including substitution of solvents and co-reagents are within the ability of the skilled artisan.

Furthermore, the skilled artisan will appreciate that in some circumstances, the order in which moieties are introduced is not critical. The particular order of steps required to produce the compounds of Formula I or Formula II is dependent upon the particular compound being synthesized, the starting compound, and the relative lability of the substituted moieties, as is well appreciated by the skilled chemist. The skilled artisan will appreciate that not all substituents are compatible with all reaction conditions. These compounds may be protected or modified at a convenient point in the synthesis by methods well known in the art. The intermediates and final products of the present invention may be further purified, if desired by common techniques such as recrystallization or chromatography over solid supports such as silica gel or alumina.

The compounds of the present invention are preferably formulated as radiopharmaceutical compositions administered by a variety of routes. Preferably, such compositions are for intravenous use, preferably in humans. Such pharmaceutical compositions and processes for preparing same are well known in the art. See, e.g., Remington: The Science and Practice of Pharmacy (P. P. Gerbino, 21$^{st}$ ed., Lippincott Williams & Wilkins, 2006). Methods of using tau imaging agents for PET imaging of tau are known to those of skill in the art. See e.g. [(18)F]T807, a novel tau positron emission tomography imaging agent for Alzheimer's disease. Xia C F, et al., Alzheimer's Dement. 2013 November; 9(6):666-76.). [(18)F]T807 is also known as [18F]AV-1451.

Preferred formulations of the present invention are preparations of Compound 8 prepared from a compound of formula Ia. Particularly preferred is Compound 8 prepared from the compound of formula Ia according to the procedures described herein according to Scheme 2. Particularly preferred is Compound 8 prepared from the compound of formula Ia according to the procedures described herein according Example 2. A preferred formulation of Compound 8 is formulated in 10% EtOH (v/v), 0.45% (w/v) sodium ascorbate in 0.9% sodium chloride, preferably for use in humans. Another embodiment of the invention is a formulation of Compound 8 prepared from the compound of formula Ia and formulated in 10% EtOH (v/v), 0.45% (w/v) sodium ascorbate in 0.9% sodium chloride. Particularly preferred is Compound 4 prepared according to the procedures described herein according to Scheme 1. Particularly preferred is Compound 8 prepared from the compound of formula Ia according to the procedures described herein according to Example 2 and formulated in 10% EtOH (v/v), 0.45% (w/v) sodium ascorbate in 0.9% sodium chloride. The present invention provides a method of imaging tau comprising introducing into a mammal a detectable quantity of a diagnostic composition as described according to the embodiments herein, and allowing sufficient time for said diagnostic composition to become associated with tau; and detecting the diagnostic composition. Particularly preferred is a method of imaging tau comprising introducing into a mammal a detectable quantity of a diagnostic composition of Compound 8, prepared from the compound of formula Ia according to the procedures described herein according to Example 2, and formulated in 10% EtOH (v/v), 0.45% (w/v) sodium ascorbate in 0.9% sodium chloride.

Novel compounds of Formula I and II have been discovered to be surprisingly and unexpectedly advantageous for tau imaging, preferably including human clinical imaging. A preferred compound, the compound of formula I, also referred to herein as Compound 8, possesses a combination of particularly useful properties for tau imaging, including high affinity for tau, selectivity, uptake, washout, and metabolic profile. In vivo Compound 8 demonstrates advantageous tissue distribution, pharmacokinetics, and metabolic stability. Ex vivo and/or in vitro, Compound 8 demonstrates high affinity binding to tau, and labels tau containing tissue samples from AD brain with high selectivity with respect to Aβ and/or non-tau binding. Compound 8 demonstrates high affinity and selectivity for tau, exhibiting radiographic signals which are disease state, tissue, and cellular location specific. The radiographic signals generated by Compound 8 reflect improved detection of tau as compared to undesired non-tau signals, and an in vivo tissue distribution and metabolic profile which are useful for a clinical radiopharmaceutical imaging agent. Compound 8, having this combination of particularly useful properties, provides for enhanced tau images, as compared with known agents, producing images with improved clarity due to robust tau signals and decreased non-tau signals. This surprisingly advantageous combination of properties provides an effective clinical tau imaging agent which facilitates imaging of patients for tau. The use of Compound 8 in clinical tau PET imaging would have important positive impact on assessment and or diagnosis of AD, and would advance the detection, treatment, monitoring, and evaluation of tau and diagnosis of diseases involving tau.

EXAMPLES AND PREPARATIONS

General Methods

Figure 1:
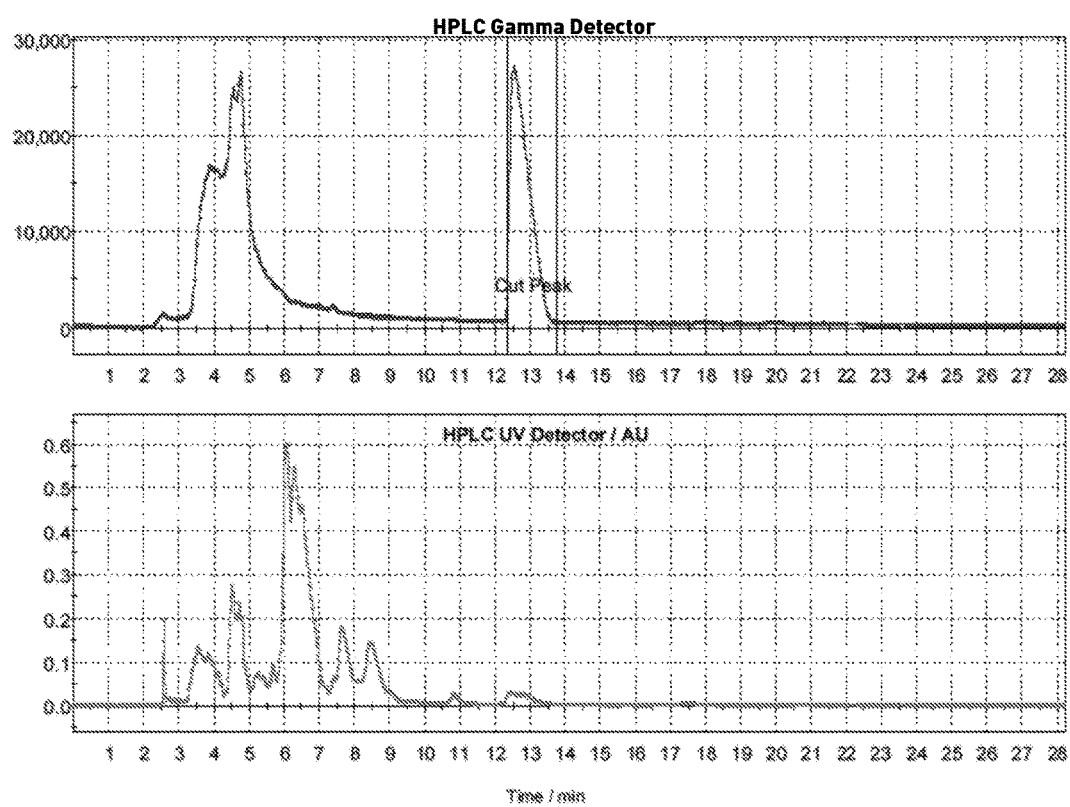
FIG. 1. Representative Semi-Preparative HPLC Chromatogram of 3-(3-[18F]-Fluoroazetidin-1-yl)-8-methyl-benzo[4,5]imidazo[1,2-a]pyridine (Compound 8) Radiosynthesis. The upper panel illustrates an HPLC chromatograph with gamma detection. The lower panel illustrates an HPLC chromatograph with UV detection. The segment indicated as "Cut Peak" indicates the corresponding fractions collected to obtain the product 3-(3-[18F]-Fluoroazetidin-1-yl)-8-methylbenzo[4,5]imidazo[1,2-a]pyridine (Compound 8).

All reactions are run under a nitrogen atmosphere unless otherwise noted. Products are purified using an automated Teledyne Isco Flash® Chromatography System. 1H, 19F, and $^{13}$C NMR spectra are recorded on a Bruker® HD Avance III 400 spectrometer in CDCl$_3$ (Cambridge Isotope Laboratories. Cat. No. DLM-7-100) or DMSO-d6, (Cambridge Isotope Laboratories, Cat. No. DLM-10-25). HRMS data are obtained on a Waters® QTof mass spectrometer using an electrospray ionization positive scan mode. Elemental analysis is performed at Galbraith Laboratories using GLI Procedure ME-14 (Galbraith Inc., 2323 Sycamore Drive, Knoxville. Tenn. 37921). Reagents, solvents, and supplies are known to the skilled chemist. The names for the compounds of the present invention can be generated for example using Symyx Version 3.2.NET with the IUPAC naming functionality.

Abbreviations represent the common and ordinary usage known to one of skill in the art and particular abbreviations used herein have the following meanings:

Abbreviations

BPV bulk product vial
bs Broad singlet
CDCl$_3$ deuterated chloroform
CH$_2$Cl$_2$ methylene chloride
d doublet
DAD diode array detector
dd doublet of doublets
dt doublet of triplets
DMPAO [(2,6-dimethylphenyl)amino](oxo)acetic acid
DMSO dimethyl sulfoxide
DMSO-d6 hexadeuterodimethyl sulfoxide
EtOH ethanol
HPLC high performance liquid chromatography
HRMS high resolution mass spectrometry
IHC immunohistochemistry
K$_2$CO$_3$ potassium carbonate
LCMS liquid chromatography mass spectrometry
N normal
NMR nuclear magnetic resonance
PHF paired helical filaments
ppm parts per million
QTof quaternary time of flight
s singlet
SUV standardized uptake value
SUVr standardized uptake value ratio
t triplet
UPLC ultra-high performance liquid chromatography
PBS phosphate buffered saline
WFI water for injection Schemes Scheme 1 provides the synthesis of 3-(3-fluoroazetidin-1-yl)-8-methylbenzo[4,5]imidazo[1,2-a]pyridine. The synthesis commences with the formation of the benzo[4,5]imidazol[1,2-a]pyridine core via a copper catalyzed coupling of commercially available 2-bromo-4-methylaniline and 2,4-dibromopyridine followed by intramolecular cyclization. The desired product, 3-(3-fluoroazetidin-1-yl)-8-methylbenzo[4,5]imidazo[1,2-a]pyridine, is obtained via a second copper catalyzed coupling of 3-bromo-8-methylbenzo[4,5]imidazo[1,2-a]pyridine (3) and 3-fluoroazetidine hydrogen chloride. After column chromatography on silica gel, metal scavenging with Quadrasil MP resin, and trituration, 3-(3-fluoroazetidin-1-yl)-8-methylbenzo[4,5]imidazo[1,2-a]pyridine (Compound 4) is obtained as a yellow solid (4.44 g, 21% overall yield).

Scheme 1: Synthesis of 3-(3-Fluoroazetidin-1-yl)-8-methylbenzo[4,5]imidazo[1,2-a]pyridine.

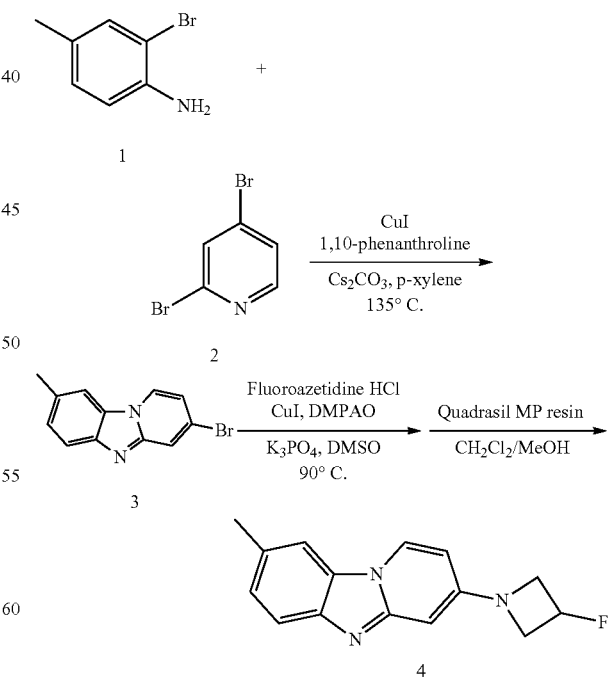

Scheme 2 provides the synthesis of 1-(8-methylbenzo[4,5]imidazo[1,2-a]pyridin-3-yl)azetidin-3-yl 4-methylbenzenesulfonate, which is the precursor for 3-(3-[18F]-fluoroazetidin-1-yl)-8-methylbenzo[4,5]imidazol[1,2-a]pyridine. Copper catalyzed coupling of 3-bromo-8-methylbenzo[4,5] imidazo[1,2-a]pyridine (3) and 3-hydroxyazetidine affords hydroxyl intermediate 1-(8-methylbenzo[4,5]imidazo[1,2-a]pyridin-3-yl)azetidin-3-ol (5), which is also purified by silica gel column chromatography. The clean intermediate is then reacted with tosyl anhydride and triethylamine, followed by silica gel column chromatography to give the desired product, 1-(8-methylbenzo[4,5]imidazo[1,2-a]pyridin-3-yl)azetidin-3-yl 4-methylbenzenesulfonate (6), as a beige solid (3.21 g, 31% overall yield).

Scheme 2: Synthesis of 1-(8-Methylbenzo[4,5]imidazo[1,2-a]pyridin-3-yl)azetidin-3-yl 4-methylbenzenesulfonate (6).

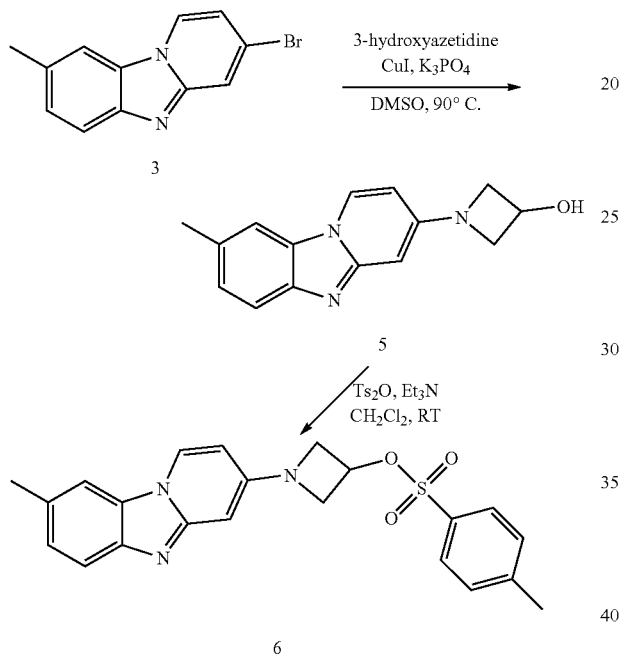

As per Scheme 3, 3-(3-[18F]-fluoroazetidin-1-yl)-8-methylbenzo[4,5]imidazo[1,2-a]pyridine. Compound 8, is prepared from a compound of Formula 7 where R is a suitable leaving group. More specifically, a compound of Formula 7 where R is a leaving group such as methanesulfonyl (mesyl) or 4-methylbenzenesulfonyl (tosyl), can be reacted with a suitable source of $^{18}F$ fluoride ($[^{18}F]F^-$) in the presence of a suitable base such as potassium carbonate. Sources of $^{18}F$ fluoride ($[^{18}F]F^-$) include $[^{18}F]F$ $K_{222}$. Suitable solvents include dimethylsulfoxide.

Scheme 3: Synthesis of 3-(3-[18F]-Fluoroazetidin-1-yl)-8-methylbenzo[4,5]imidazo[1,2-a]pyridine (8).

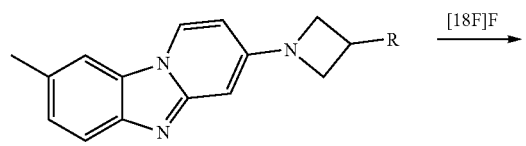

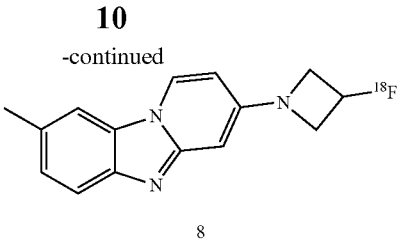

Example 1

Synthesis of 3-(3-Fluoroazetidin-1-yl)-8-methylbenzo[4,5]imidazo[1,2-a]pyridine (Compound 4)

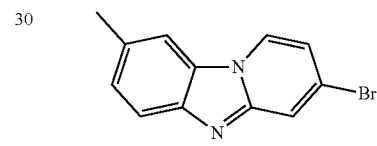

Step 1: Synthesis of 3-Bromo-8-methylbenzo[4,5]imidazo[1,2-a]pyridine (Compound 3)

In a 1 L round-bottom flask are combined 2,4-dibromopyridine (20.0 g, 84.6 mmol), copper iodide (3.22 g, 16.9 mmol), 1,10-phenanthroline (6.10 g, 33.8 mmol), cesium carbonate (110 g, 338 mmol), Celite (16 g) and p-xylene (170 mL). To the resulting slurry is added 2-bromo-4-methylaniline (10.6 mL, 84.6 mmol) and nitrogen is bubbled through the vigorously stirred mixture for 10 minutes. The flask is fitted with a reflux condenser and the system is heated at 135° C. for 24 hours. The reaction mixture is cooled to room temperature and filtered. The filter cake is rinsed with methylene chloride and ethyl acetate, and the combined organic filtrates are concentrated under reduced pressure over silica gel. The crude reaction product is purified by chromatography on silica gel using a gradient of 0 to 10% ethyl acetate in methylene chloride. The resulting brown solid is slurried in methylene chloride and triturated using hexanes, then isolated by filtration to provide the title compound (6.52 g, 25.0 mmol, 30% yield) as a shiny yellow solid: $^1H$ NMR (400.13 MHz, DMSO-$d_6$ with TFA-d) δ ppm: 9.40 (dd, J=0.9, 7.2 Hz, 1H), 8.45 (dd, J=0.7, 1.8 Hz, 1H), 8.42 (bs, 1H), 7.86 (dd, J=2.1, 7.3 Hz, 1H), 7.83 (d, J=8.4 Hz, 1H), 7.64 (dd, J=0.9, 8.4 Hz, 1H), 2.57 (s, 3H); $^{13}C$ NMR (100.62 MHz, DMSO-$d_6$ with TFA-d) δ ppm 142.6, 134.6, 131.9, 130.8, 129.9, 129.4, 127.0, 119.7, 115.0, 113.8, 113.4, 21.1; HRMS (m/z): found: 261.0013 (M+H), calcd for $C_{12}H_{10}N_2Br$: 261.0027, Err=−5.4 ppm.

Step 2: Synthesis of 3-(3-Fluoroazetidin-1-yl)-8-methylbenzo[4,5]imidazo[1,2-a]pyridine (Compound 4)

To a solid mixture of 3-bromo-8-methylbenzo[4,5]imidazo[1,2-a]pyridine (6.52 g, 25.0 mmol), 3-fluoroazetidine hydrochloride (3.90 g, 35.0 mmol), copper (I) iodide (475 mg, 2.50 mmol), [(2,6-dimethylphenyl)amino](oxo)acetic acid (DMPAO, 963 mg, 4.99 mmol) and potassium phosphate (15.9 g, 74.9 mmol) is added dimethylsulfoxide (110 mL). Stirring is initiated and nitrogen bubbled through the slurry for 15 minutes. The system is fitted with a reflux condenser, the headspace flushed with nitrogen, and the mixture heated at 90° C. for 48 hours. Additional 3-fluoroazetidine hydrochloride (1.39 g, 12.5 mmol), copper (I) iodide (166 mg, 0.871 mmol), DMPAO (344 mg, 1.78 mmol) and potassium phosphate (5.56 g, 26.2 mmol) are added and stirring continued at 90° C. for an additional 24 hours. The reaction mixture is cooled to room temperature and added slowly to water (1000 mL) with vigorous stirring. The precipitated solids are isolated by vacuum filtration, and the aqueous filtrate extracted with 10% methanol in methylene chloride (3×250 mL). The organic extracts are combined with the isolated solids from the initial aqueous filtration, dried over sodium sulfate, and concentrated under reduced pressure. The isolated crude solids (6.46 g) are preabsorbed onto silica gel (40 g) and purified by chromatography on silica gel using a gradient of 0 to 20% ethyl acetate in methylene chloride followed by a gradient of 0 to 10% methanol in methylene chloride. The pooled fractions are concentrated and the resulting dark yellow solids (5.43 g) are suspended and sonicated in methylene chloride (40 ml). Diethyl ether (800 mL) is added and the bright yellow solid is isolated by filtration, washed with additional diethyl ether (400 mL), and dried under high vacuum. A solution of the isolated product (4.62 g) in 10% methanol/methylene chloride (200 mL) is treated with Quadrasil MP resin (1.60 g), and the slurry is stirred for 2 hours at room temperature. The slurry is filtered and the solids rinsed with methanol/methylene chloride (100 mL). The combined organics are concentrated under reduced pressure, and the resulting solid is suspended in methylene chloride, sonicated, and triturated from diethyl ether (750 mL). The precipitated solids are collected by vacuum filtration, rinsed with diethyl ether, and dried under vacuum to afford the title compound as a yellow powder (4.44 g, 17.4 mmol, 70% yield over 2 steps): $^1$H NMR (400.13 MHz, CDCl$_3$) δ ppm: 8.11 (dd, J=0.7, 7.5 Hz, 1H), 7.63 (d, J=8.3 Hz, 1H), 7.47-7.48 (m, 1H), 7.23 (ddd, J=0.5, 1.5, 8.3 Hz, 1H), 6.26 (d, 2.1 Hz, 1H), 6.13 (dd, J=2.5, 7.3 Hz, 1H), 5.35-5.54 (m, 1H), 4.24-4.34 (m, 2H), 4.07-4.17 (m, 2H), 2.53 (s, 3H); $^{13}$C NMR (100.62 MHz, CDCl$_3$) δ ppm: 150.7, 150.3 (d, J=1.5 Hz), 143.7, 129.5, 129.0, 126.5, 125.5, 118.1, 109.4, 101.0, 91.6, 82.2 (d, J=206.9 Hz), 59.1 (d, J=24.9 Hz), 21.8; $^{19}$F NMR (376.44 MHz, CDCl$_3$) δ ppm: −180.4; HRMS (m/z): found: 256.1244 (M+H), calcd for C$_{15}$H$_{15}$N$_3$F: 256.1250. Err=−2.3 ppm; Elemental Analysis (GLI Procedure ME-14): Calcd for C$_{15}$H$_{14}$FN$_3$C, 70.57; H, 5.53; N, 16.46. Found C, 70.17; H, 5.68; N, 16.43, max diff=0.41.

Preparation 1

Synthesis of 1-(8-Methylbenzo[4,5]imidazo[1,2-a]pyridin-3-yl)azetidin-3-yl 4-methylbenzenesulfonate (Compound 6)

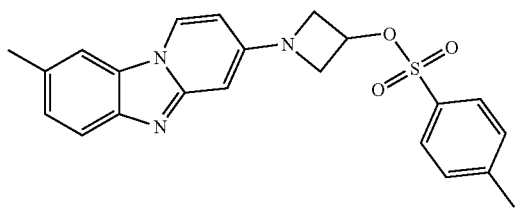

Step 1: Synthesis of 1-(8-Methylbenzo[4,5]imidazo[1,2-a]pyridin-3-yl)azetidin-3-ol (Compound 5)

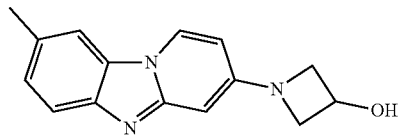 [SMILES: Cc1ccc2nc3cc(N4CC(O)C4)ccn3c2c1]

To a solid mixture of 3-bromo-8-methylbenzo[4,5]imidazo[1,2-a]pyridine (6.57 g, 25.2 mmol), azetidin-3-ol hydrochloride (5.52 g, 50.4 mmol), copper (I) iodide (480 mg, 2.52 mmol), [(2,6-dimethylphenyl)amino](oxo)acetic acid (DMPAO, 972 mg, 5.04 mmol) and potassium phosphate (21.4 g, 101 mmol) is added dimethylsulfoxide (110 mL). Stirring is initiated and nitrogen bubbled through the slurry for 15 minutes. The system is fitted with a reflux condenser, the headspace flushed with nitrogen, and the mixture heated at 90° C. for 24 hours. The reaction mixture is cooled to room temperature and added slowly to water (1000 mL) with vigorous stirring. The precipitated solids are isolated by vacuum filtration and dissolved in 10% methanol in methylene chloride (500 mL). The aqueous filtrate is extracted with 10% methanol in methylene chloride (3×250 mL). The organic extracts are combined with the solution of isolated solids from the initial aqueous filtration and the mixture is dried over sodium sulfate, filtered and concentrated under reduced pressure. The resulting solid is dissolved in methylene chloride, preabsorbed onto silica gel and purified by chromatography on silica gel using a gradient of 0 to 30% methanol in methylene chloride to afford the title product as a grey-green solid (3.18 g, 50%): $^1$H NMR (400.13 MHz, DMSO-d with TFA-d) δ ppm: 8.95 (d, J=7.6 Hz, 1H), 8.06 (s, 1H), 7.51 (d, J=8.2 Hz, 1H), 7.36 (dd, J=0.9, 8.3 Hz, 1H), 6.76 (dd, J=2.3, 7.5 Hz, 1H), 6.27 (d, J=2.1 Hz, 1H), 4.66-4.71 (m, 1H), 4.38-4.41 (m, 2H), 3.92-3.95 (m, 2H), 2.48 (s, 3H); $^{13}$C NMR (100.62 MHz, DMSO-d$_6$ with TFA-d) δ ppm: 153.6, 144.6, 132.4, 129.5, 128.6, 128.1, 126.9, 112.0, 111.9, 104.3, 83.3, 61.0, 60.16, 21.0; HRMS (m/z): found: 254.1296 (M+H), calcd for C$_{15}$H$_{16}$N$_3$O: 254.1293, Err=1.2 ppm.

Step 2: 1-(8-Methylbenzo[4,5]imidazo[1,2-a]pyridin-3-yl)azetidin-3-yl 4-methylbenzenesulfonate (Compound 6)

A suspension of 1-(8-methylbenzo[4,5]imidazo[1,2-a]pyridin-3-yl)azetidin-3-ol (Compound 5) (3.18 g, 12.6 mmol) in dichloromethane (135 mL) is treated with triethylamine (17.5 mL, 126 mmol), stirred for 10 minutes, and p-toluenesulfonic anhydride (12.31 g, 37.7 mmol) is then added. The reaction is stirred at room temperature for 22 hours. Additional p-toluenesulfonic anhydride (1.84 g, 5.6 mmol) is added and the reaction stirred 6 hours. The reaction mixture is concentrated, resuspended in methylene chloride (175 mL), and treated with 1 N aqueous sodium hydroxide solution (150 mL). The mixture is stirred vigorously for 1.5 hours, transferred to a separatory funnel and the layers are separated. The organic layer is vigorously shaken with 1 N aqueous sodium hydroxide solution (2×100 mL, 1×150 mL). The organic layer is dried over magnesium sulfate, filtered, concentrated, and dried under high vacuum. A solution of the isolated brown solid in 10% methanol in methylene chloride is concentrated over silica gel (24 g) under reduced pressure. The title compound is purified by chromatography on silica gel using a gradient of 0 to 10% methanol in methylene chloride. The resulting solid is suspended in methylene chloride (ca. 50 mL), sonicated, and triturated with diethyl ether (750 mL). The precipitated solids are collected by filtration, rinsed with diethyl ether, and dried under vacuum to afford 1-(8-methylbenzo[4,5]imidazo[1,2-a]pyridin-3-yl)azetidin-3-yl 4-methylbenzenesulfonate as a beige solid (3.21 g, 7.89 mmol, 63% yield): $^1$H NMR (400.13 MHz, DMSO-$d_6$ with TFA-d) δ ppm: 9.01 (d, J=7.7 Hz, 1H), 8.11 (bs, 1H), 7.85-7.88 (m, 2H), 7.52-7.55 (m, 3H), 7.39 (dd, J=1.0, 8.3 Hz, 1H), 6.82 (dd, J=2.2, 7.5 Hz, 1H), 6.38 (d, J=2.3 Hz, 1H), 5.32-5.37 (m, 1H), 4.94-4.54 (m, 2H), 4.21-4.25 (m, 2H), 2.46 (s, 3H): $^{13}$C NMR (100.62 MHz, DMSO-$d_6$ with TFA-d) δ ppm: 153.3, 145.6, 144.3, 132.6, 132.2, 130.4, 129.5, 128.7, 128.3, 127.7, 126.9, 112.2, 112.0, 104.4, 84.4, 68.5, 58.4, 21.1, 21.0; HRMS (m/z): found: 408.1401 (M+H), calcd for $C_{15}H_{16}N_3O$: 408.1382, Err=4.7 ppm: Elemental Analysis (GLI Procedure ME-14): Calcd for $C_{22}H_{21}N_3O_3S$ C, 64.85; H, 5.19; N, 10.31. found C, 64.38; H, 5.27; N, 10.27, max diff=0.48.

Example 2

Synthesis of 3-(3-[18F]-Fluoroazetidin-1-yl)-8-methylbenzo[4,5]imidazol[1,2-a]pyridine (Compound 8)

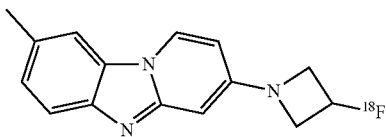 [SMILES: Cc1ccc2nc3cc(N4CC([18F])C4)ccn3c2c1]

The synthesis of 3-(3-[18F]-Fluoroazetidin-1-yl)-8-methylbenzo[4,5]imidazo[1,2-a]pyridine is performed using a GE TRACERlab $FX_{F-N}$ automated radiosynthesizer with a starting activity of 1-2 Ci. A typical synthesis time is ~60±5 minutes and the range of decay corrected yield is 22-44%. [$^{18}$F]Fluoride activity is retained on a Sep-Pak Accell Plus QMA Carbonate Plus Light Cartridge (46 mg Sorbent per Cartridge, 40 μm Particle Size, Waters Part No. 186004540) and eluted to the reaction vessel using 0.8 mL of an aqueous Cryptand 2.2.2-$K_2CO_3$ solution [Cryptand 2.2.2 (7 mg) and potassium carbonate (0.75 mg) in acetonitrile (0.4 mL) and WFI (water for injection, 0.4 mL), respectively]. The eluted activity is dried by heating at 70° C. under nitrogen flow and vacuum for 4.5 minutes. The temperature is then raised to 100° C. under vacuum for 5 minutes to afford anhydrous Cryptand 2.2.2-$K_2CO_3$ [$^{18}$F]fluoride.

A solution of 1-(8-methylbenzo[4,5]imidazo[1,2-a]pyridin-3-yl)azetidin-3-yl 4-methylbenzenesulfonate [1 mg in anhydrous dimethylsulfoxide (2 mL)] is added to the reaction vessel containing the anhydrous Cryptand 2.2.2-$K_2CO_3$ [$^{18}$F]fluoride and the resulting mixture is kept at 140° C. for 10 minutes followed by hydrolysis with 1 mL of 1N sodium hydroxide at 65° C. for 3 minutes. After cooling to 60° C., the crude reaction mixture is neutralized with 2 mL of 0.5N hydrochloric acid (HCl) (1 mL of 1N HCl+1 mL WFI). The reaction crude is then loaded onto a semi-preparative HPLC column for purification using isocratic elution (See FIG. 1 for representative chromatogram). Semi-Preparative Column: Agilent ZORBAX Eclipse Plus Phenyl-Hexyl, Custom PN, 5 μm, 9.4 mm×250 mm, flow rate=4 mL/min; 280 nm; retention time ~12-13 minutes. Mobile Phase Composition: 76% 9 mM HCl in WFI (3 mL of 3N HCl in 1 L of WFI), 24% Acetonitrile (HPLC grade).

Figure 2:
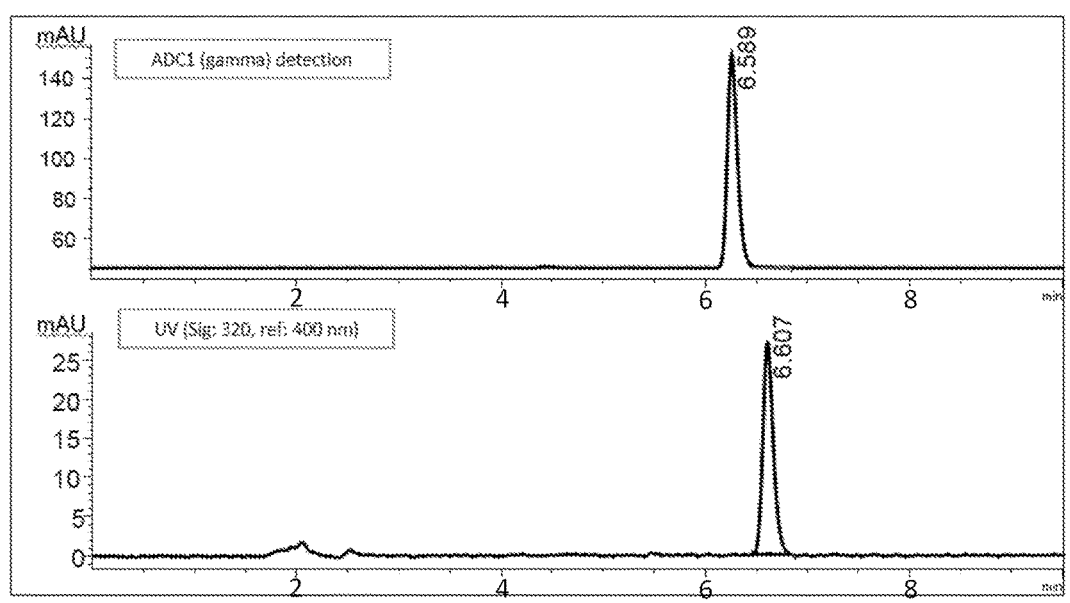
FIG. 2. Representative Analytical HPLC (QC) Chromatogram of 3-(3-[18F]-Fluoroazetidin-1-yl)-8-methylbenzo[4,5]imidazo[1,2-a]pyridine (Compound 8). The upper panel labelled (HPLC Gamma Detector) illustrates a radio-chromatogram of 3-(3-[18F]-Fluoroazetidin-1-yl)-8-methyl-benzo[4,5]imidazo[1,2-a]pyridine (Compound 8). The lower panel labelled (HPLC UV Detector) illustrates an ultraviolet chromatogram of 3-(3-[18F]-Fluoroazetidin-1-yl)-8-methylbenzo[4,5]imidazo[1,2-a]pyridine (Compound 8). The peak retention time of 6.589 minutes is indicated on the main peak in the upper panel, and peak retention time of 6.607 minutes is indicated on the main peak in the lower panel.

The HPLC fraction containing the purified 3-(3-[18F]-fluoroazetidin-1-yl)-8-methylbenzo[4,5]imidazo[1,2-a]pyridine is diluted with 0.5% (w/v) sodium ascorbate in WFI (40 mL). The diluted solution is then passed through a Sep-Pak® C18 Plus Light Cartridge (130 mg Sorbent per Cartridge, 55-105 μm Particle Size, Waters Part No. WAT023501; conditioned with ethanol (5 mL) then WFI (5 mL) prior to use) and the retained 3-(3-[18F]-fluoroazetidin-1-yl)-8-methylbenzo[4,5]imidazo[1,2-a]pyridine is washed with 0.5% (w/v) sodium ascorbate in water for injection solution (10 mL). 3-(3-[18F]-fluoroazetidin-1-yl)-8-methylbenzo[4,5]imidazo[1,2-a]pyridine is eluted off the C18 cartridge using dehydrated alcohol, USP (1 mL) into a flask containing 7 mL of 0.5% (w/v) sodium ascorbate in 0.9% sodium chloride for injection, USP. The C18 cartridge is then rinsed with an additional 2 mL of 0.5% (w/v) sodium ascorbate in 0.9% sodium chloride for injection, USP. The resulting solution (total 10 mL) is sterile filtered through a 0.22 μm Millex GV PVDF filter (Millipore SLGV013SL) into the bulk product vial (BPV: 30 mL Sterile Empty Vial from Allergy Laboratories with a 20 mm chlorobutyl stopper). A sample from the BPV is taken out for quality control (see FIG. 2 for representative chromatogram) by HPLC using the gradient method detailed in Table 1 below.

TABLE 1

Analytical HPLC Method[A.] for 3-(3-[18F]-Fluoroazetidin-1-yl)-8-methylbenzo[4,5]imidazo[1,2-a]pyridine.

| Minute | 0.1% (v/v) TFA in $H_2O$ | Acetonitrile |
|---|---|---|
| 0 | 75% | 25% |
| 12 | 50% | 50% |
| 13 | 0% | 100% |
| 16 | 0% | 100% |
| 17 | 75% | 25% |
| 20 | 75% | 25% |

[A.]Analytical column conditions as follows: Agilent ZORBAX Eclipse XDB-C18 4.6 mm × 150 mm, Part No. 993967-902, flow rate = 1 mL/mm; UV = 320 nm.

Preliminary stability of 3-(3-[18F]-fluoroazetidin-1-yl)-8-methylbenzo[4,5]imidazo[1,2-a]pyridine (Compound 8) formulations are evaluated. Samples from batches (size ranging from 235 mCi to 471 mCi) are taken and analyzed by HPLC for radiochemical purity over an 6 hour time period. Batches formulated with sodium ascorbate retain 96-97% purity up to 6 hours, while the batch formulated without sodium ascorbate deteriorates over time and degrades by 5 hours. See Table 2 for details.

TABLE 2

3-(3-[18F]-Fluoroazetidin-1-yl)-8-methylbenzo[4,5]imidazo[1,2-a]pyridine Stability Results.

| Batch Size (DCY) | Formulation | Strength (mCi/mL) | Stability Results (% RCP) | | | |
|---|---|---|---|---|---|---|
| | | | $T_0$ | $T_{0+2 h}$ | $T_{0+4 h}$ | $T_{0+6 h}$ |
| 235 mCi (23%) | 10% EtOH (v/v), 0.45% (w/v), | 23.5 | 98 | 97 | 97 | 97 |
| 337 mCi (24%) | Sodium Ascorbate in 0.9%, | 33.7 | 98 | 97 | 96 | 96 |
| 295 mCi (22%) | Sodium Chloride Injection, USP | 14.8 | 97 | 96 | 96 | 96 |
| 471 mCi (44%) | 10% EtOH (v/v) in 0.9% Sodium Chloride Injection, USP | 47.1 | 89 | 89 | 80 | 0 (5 h) |

Assay Example 3

Ki Determination of 3-(3-fluoroazetidin-1-yl)-8-methylbenzo[4,5]imidazo[1,2-a]pyridine versus [18F]AV-1451, and Kd of 3-(3-[18F]-fluoroazetidin-1-yl)-8-methylbenzo[4,5]imidazo[1,2-a]pyridine, Using Tau from Alzheimer's Disease Donors PHF Preparation:

Purified, soluble PHF is isolated from AD brain tissue using a protocol modified from the procedure described by Jicha, et al. (G. A. Jicha, A. O'Donnell, C. Weaver (1999) "Hierarchical phosphorylation of recombinant tau by the paired-helical filament-associated protein kinase is dependent on cyclic AMP-dependent protein kinase" J Neurochem. 72(1):214). Briefly, AD cortex is homogenized using a handheld Kinematica Polytron, followed by high pressure batch—gas expansion using a Parr Cell disruption bomb. Crude homogenate is centrifuged at 28 kg to pellet cell debris. Soluble PHF is isolated from the supernatant by affinity chromatography over an Affigel-10 column on which the tau antibody MCI, which recognizes a pathological conformation of tau, has been immobilized (G. A. Jicha, R. Bowser, I. G. Kazam (1997), "Alz-50 and MC-1, a new monoclonal antibody raised to paired helical filaments, recognize conformational epitopes on recombinant tau" J Neurosci Res. 48(2): 12.)

3-(3-Fluoroazetidin-1-yl)-8-methylbenzo[4,5]imidazo[1,2-a]pyridine Ki Determination The IC50 (i.e. the molar concentration of competing ligand which reduces the specific binding of a radioligand by 50%) for the unlabeled compound is determined by competition radioligand binding, in which the binding of [18F]AV-1451 to PHF is competed with unlabeled compound at various concentrations. The reaction mixture (200 µl) contains PHF (0.12 ug), [18F]AV-1451 at 0.1-0.5 nM, and cold compound serially diluted from 316 nM to 0.01 nM; assays are performed in PBS, pH 7.4 containing 0.01% bovine serum albumin in 96 well polypropylene microplates. Non-specific binding is defined as the binding of the radioligand in the presence of T808/AV-680 (5 µM), a known PHF ligand (Zhang, J. (2012), "A highly selective and specific PET tracer for imaging of tau pathologies" J Alzheimers Dis., 31(3):601). After incubation for 1.5 h at 37° C., the bound radioactivity is harvested onto Millipore MultiScreen$^{HTS}$ 96-well glass fiber FB filter plates using a Millipore MultiScreen$^{HTS}$ Vacuum Manifold, followed by five washes with PBS, pH 7.4. Filters containing bound [18F]AV-1451 are assayed for radioactivity in a Wizard 2480 automatic gamma-counter [Perkin Elmer]. Using these assay conditions, the total bound fraction is typically less than 10% of the added radioligand. The IC50 is determined using an ActivityBase or XLfit model 205 (or a comparable model) in which:

$y=A+(B-A)/(1+((C/x)^D)$

Y=% Inhibition
X=Concentration of the cold competing ligand (nM)
A=minimum Y (0%)
B=maximum Y (100%)
C=IC50
D=Slope factor The Ki (i.e. the equilibrium dissociation constant for binding of the unlabeled compound) is calculated from the IC50 value using the Cheng-Prusoff equation (Cheng Y., Prusoff W. H. (1973), "Relationship between the inhibition constant (KI) and the concentration of inhibitor which causes 50 percent inhibition (150) of an enzymatic reaction" Biochem Pharmacol 22 (23):3099-3108):

$Ki=IC50/(1+[L]/Kd)$

[L]=the concentration of [18F]AV-1451 (typically ~0.5 nM)
$K_d$=the dissociation constant for [18F]AV-1451 (0.57 nM).

The Ki versus [18F]AV-1451 for 3-(3-fluoroazetidin-1-yl)-8-methylbenzo[4,5]imidazo[1,2-a]pyridine is 0.6 nM on tau that is obtained from donors with Alzheimer's disease indicating that this compound binds tau. Therefore, PET imaging with Compound 8 and examination of the imaging pattern would be useful to detect the presence of tau in patients and could confirm a diagnosis of AD or non-AD tauopathies.

3-(3-[18F]-Fluoroazetidin-1-yl)-8-methylbenzo[4,5]imidazo[1,2-a]pyridine Kd Determination The dissociation constant [Kd] for the radiolabeled compound 3-(3-[18F]-fluoroazetidin-1-yl)-8-methylbenzo[4,5]imidazol[1,2-a]pyridine is determined by saturation binding, in which the total and nonspecific binding of the radioligand are measured at various radioligand concentrations. The reaction mixture (250 µl) contains PHF (150 0.15 µg), and 3-(3-[18F]-fluoroazetidin-1-yl)-8-methylbenzo[4,5]imidazol[1,2-a]pyridine, serially diluted from 25 nM to 0.3 nM in PBS: assays are performed in PBS containing 0.01% bovine serum albumin in 96 well polypropylene microplates. Nonspecific binding is defined as the binding of the radioligand in the presence of T808/AV-680 (10 µM). After incubation for 1.5 h at 37° C., the bound radioactivity is harvested by vacuum filtration onto Millipore MultiScreenHTS 96-well glass fiber FB filter plates, using a Millipore MultiScreenHTS Vacuum Manifold, followed by five washes with PBS. Filters containing bound 3-(3-[18F]-fluoroazetidin-1-yl)-8-methylbenzo[4,5]imidazo[1,2-a]pyridine are assayed for radioactivity in a Wizard 2480 automatic gamma-counter [Perkin Elmer]. Using these assay conditions, the total bound fraction is typically less than 10% of the added radioligand. The total binding and nonspecific binding data are analyzed by nonlinear regression analysis using Graphpad Prism to determine the Kd for the radioligand.

The Kd of 3-(3-[18F]-fluoroazetidin-1-yl)-8-methylbenzo[4,5]imidazo[1,2-a]pyridine is 0.85±0.02 nM on tau that is obtained from donors with Alzheimer's disease, indicating that this compound binds tau with high affinity. Therefore, PET imaging with Compound 8 and examination of the imaging pattern would be useful to detect the presence of tau in patients and could confirm a diagnosis of AD or non-AD tauopathies.

Assay Example 4

Kd Determination for the Binding of 3-(3-[18F]-Fluoroazetidin-1-yl)-8-methylbenzo[4,5]imidazo[1,2-a]pyridine to Native Tau Aggregates in Human AD Brain Tissue Autoradiography is employed in Kd determination of 3-(3-[18F]-fluoroazetidin-1-yl)-8-methylbenzo[4,5]imidazo[1,2-a]pyridine binding to native tau-aggregates on human AD brain sections that have been characterized using anti-tau and anti-amyloid immunostaining according to methods known to the skilled artisan (See e.g. [(18)F]T807, *a novel tau positron emission tomography imaging agent for Alzheimer's disease*. Xia C F et al., *Alzheimer's Dement.* 2013 November; 9(6):666-76). (Zhang. J (2012). "*A highly selective and specific PET tracer for imaging of tau pathologies*" *J Alzheimers Dis.*, 31(3):601). The experiment uses 15 adjacent frontal lobe sections from each of two AD brains: a tau-rich and amyloid-rich (Tau+Aβ+) brain as well as tau-poor and amyloid-rich (Tau-Aβ+) brain to define non-specific binding. Sections are covered with 0.5 ml of 3-(3-[18F]-fluoroazetidin-1-yl)-8-methylbenzo[4,5]imidazo[1,2-a]pyridine, serially diluted from ~250 nM in binding buffer (2.5% dimethylsulfoxide+2.5% ethanol in PBS, pH 7.4). After a 60 min incubation at room temperature, unbound ligand is removed through successive wash cycles (2 minutes in PBS, 2 minutes 30% ethanol/PBS, 2 minutes in 70% ethanol/PBS, 2 minutes in PBS). After drying under the hood, the sections are exposed overnight to a phosphorimaging screen. The autoradiography signal recorded on the phosphorimaging screen is read using a GE Healthcare Life Sciences Typhoon FLA 7000 Phosphorimager. The signal intensity on the grey matter is measured using Fujifilm Multi Gauge software. The Kd for the compound is determined by non-linear regression analysis of the bound concentration of 3-(3-fluoroazetidin-1-yl)-8-methylbenzo[4,5]imidazo[1,2-a]pyridine versus concentration of free compound.

Figure 3:
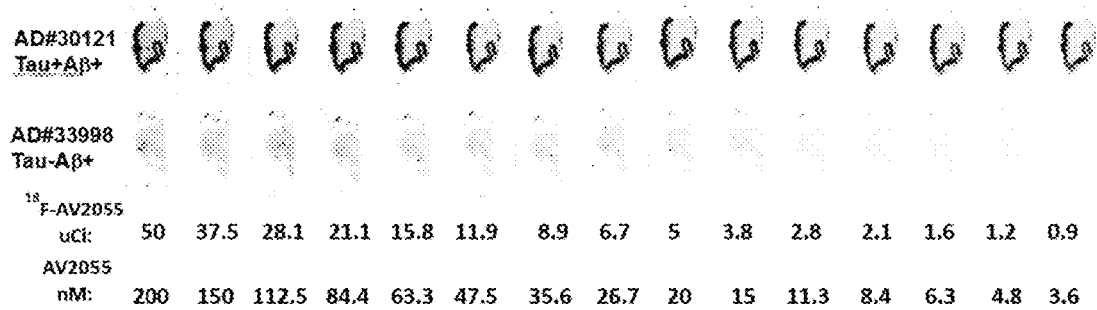
FIG. 3. 3-(3-[18F]-Fluoroazetidin-1-yl)-8-methylbenzo[4,5]imidazo[1,2-a]pyridine (Compound 8) autoradiography on AD brain sections for Kd determination. See Assay Example 4 for an explanation of the experimental setup and analysis.

Autoradiography from 3-(3-[18F]-fluoroazetidin-1-yl)-8-methylbenzo[4,5]imidazo[1,2-a]pyridine on AD brain sections for Kd determination is shown in FIG. 3. The Kd to native tau-aggregates of AD brain tissue for 3-(3-[18F]-fluoroazetidin-1-yl)-8-methylbenzo[4,5]imidazo[1,2-a]pyridine, determined by non-linear regression analysis is 2.4 nM, indicating this compound binds tau. Therefore, PET imaging with Compound 8, and examination of the imaging pattern, would be useful to detect the presence of tau in patients, and could confirm a diagnosis of AD or non-AD tauopathies.

Assay Example 5

Figure 4:
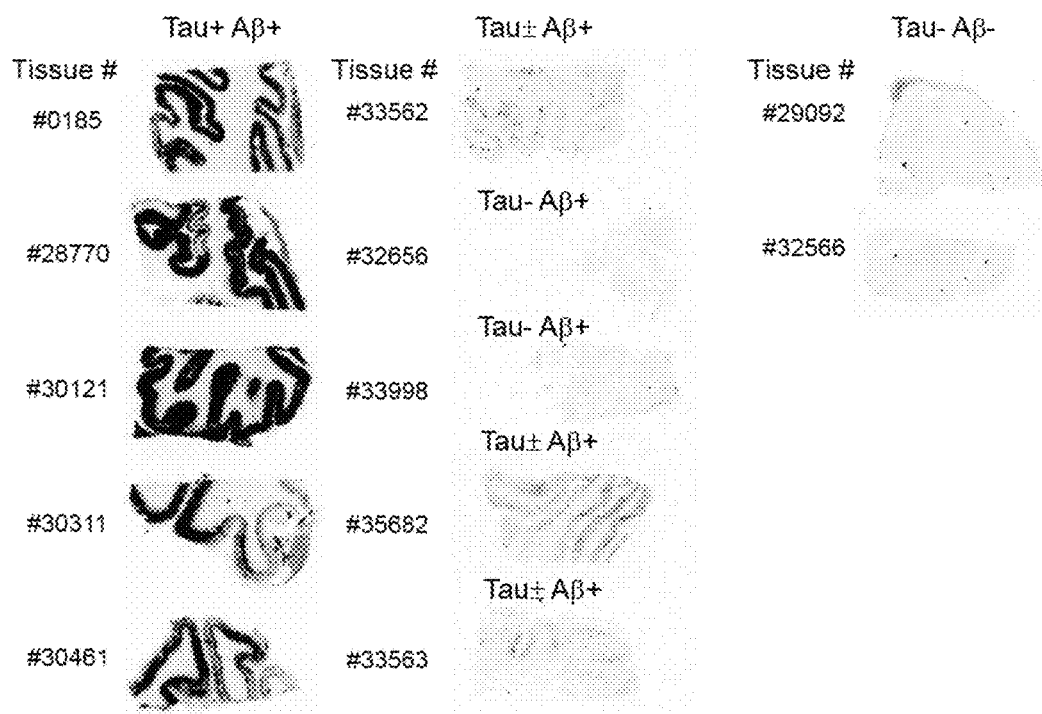
FIG. 4: 3-(3-[18F]-Fluoroazetidin-1-yl)-8-methylbenzo[4,5]imidazo[1,2-a]pyridine autoradiography on AD brain sections for selectivity determination. See Assay Example 5 for an explanation of the experimental setup and analysis.

Selectivity of 3-(3-[18F]-Fluoroazetidin-1-yl)-8-methylbenzo[4,5]imidazo[1,2-a]pyridine Towards Tau Versus β Amyloid in AD Human Brain Tissue Methods Based on the anti-tau and anti-amyloid immunostaining results of brain sections, three groups of human brain sections are selected for autoradiography experiments to determine the native tau-binding selectivity of 3-(3-[18F]-fluoroazetidin-1-yl)-8-methylbenzo[4,5]imidazo[1,2-a]pyridine. Group A are tau-rich AD brain slices (labeled as Tau+Aβ+), Group B are tau-poor AD brain slices (marked as Tau-Aβ+), and Group C are Tau-Aβ− normal brain slices. As shown in FIG. 4, Group A human AD brain sections used are #0185, #28770, #30121, #30311, and #30461. The human AD brain sections in Group B are #33562, #32656, #33998, #35682, and #33563. The normal human brain sections in group C are #29092 and #32566. Tissue slices from the same donors are used to calculate selectivity for all three compounds for testing according to Assay Example 5. Autoradiography is performed for each of these three groups of brains on adjacent 10 μm sections with the amyloid tracer [18F]W372 to quantify the β-amyloid burden. [18F]W372 is a selective amyloid binding tracer discovered by Siemens and evaluated under IND 105173. Sections are covered with 0.5 ml of 3-(3-[18F]-fluoroazetidin-1-yl)-8-methylbenzo[4,5]imidazo[1,2-a]pyridine (in 2.5:2.5:95 DMSO:EtOH:1× PBS, about 20 μCi/slide) and incubated for 1.5 hrs. Then successive washing cycles (1 min PBS, 2 min 30% EtOH/PBS, 2 min 70% EtOH/PBS, 1 min PBS) are employed to remove any unbound tracer. The sections are air dried, placed on a phosphorimaging plate (Fuji IP plate), and exposed overnight. The IP plate is read using a GE Healthcare Life Sciences Typhoon FLA 7000 Phosphorimager. The signal intensity of the grey matter is measured using Fujifilm Multi Gauge software. After subtracting the background signal (signal in the cortex region of Group C), the signal of individual sections of Group A and B are normalized with corresponding signal from autoradiography of the respective adjacent sections with [18F]W372. The calculations are based on Group B brain sections #32656 and #33998, which have undetectable tau pathology by immunohistochemistry. The normalized signal for 3-(3-[18F]-fluoroazetidin-1-yl)-8-methylbenzo[4,5]imidazo[1,2-a]pyridine in Group B brain sections is the relative signal level of 3-(3-[18F]-fluoroazetidin-1-yl)-8-methylbenzo[4,5]imidazo[1,2-a]pyridine to [F-18]W372 resulting from binding to native β-amyloid aggregates. The binding level of 3-(3-[18F]-fluoroazetidin-1-yl)-8-methylbenzo[4,5]imidazo[1,2-a]pyridine to native tau-aggregates in Group A sections is estimated by subtracting the amount of the total signal attributable to binding to 3-amyloid (calculated by multiplying the total signal from [18F]W372 binding to β-amyloid in the adjacent section by the relative signal of 3-(3-[18F]-fluoroazetidin-1-yl)-8-methylbenzo[4,5]imidazo[1,2-a]pyridine to [18F]W372 determined from the Group B sections). The resulting difference is then divided by the signal attributable to binding to β-amyloid to estimate the selectivity of 3-(3-[18F]-fluoroazetidin-1-yl)-8-methylbenzo[4,5]imidazo[1,2-a]pyridine.

The autoradiography of 3-(3-[18F]-fluoroazetidin-1-yl)-8-methylbenzo[4,5]imidazo[1,2-a]pyridine on the three groups of human brain sections is shown in FIG. 4. Strong signal on grey matter (cortex region) of sections in Group A (Tau+Aβ+) is observed, whereas in Group B (Tau-Aβ+), weak or no signal on the cortex regions of the sections is detected. No autoradiography signal is seen on the sections of the normal brains of Group C (Tau-Aβ−). These results indicate that 3-(3-[18F]-fluoroazetidin-1-yl)-8-methylbenzo[4,5]imidazo[1,2-a]pyridine binds to native tau aggregates of human AD brain specifically, and has weak or no interaction with native β-amyloid aggregates.

Since the IHC results show that Group B brain sections #32656 and #33998 are devoid of tau protein aggregates, the normalized autoradiography signal on the cortex region of these AD brain sections is derived from the binding of 3-(3-[18F]-fluoroazetidin-1-yl)-8-methylbenzo[4,5]imidazol[1,2-a]pyridine to native β-amyloid aggregates. The selectivity of 3-(3-[18F]-fluoroazetidin-1-yl)-8-methylbenzo[4,5]imidazo[1,2-a]pyridine binding to native tau aggregates vs. binding native β-amyloid aggregates is reflected by the ratio of Group A (Tau+Aβ+) signal to the signal of the brain sections #32656 and #33998.

In experiments as outlined in Assay Example 5 and shown in FIG. 4 the compound 3-(3-[18F]-fluoroazetidin-1-yl)-8-methylbenzo[4,5]imidazo[1,2-a]pyridine (Compound 8) exhibits a selectivity ratio for Tau:Aβ of approximately 26.6±4.5, based on 5 Tau+ Aβ+ brain specimens, and 2 Tau-Aβ+ brain specimens. As used in this section specimen refers to tissue samples from different donors. As outlined in Assay Example 5 and shown in FIG. 4 the compound 3-(3-[18F]-fluoroazetidin-1-yl)-8-methylbenzo[4,5]imidazo[1,2-a]pyridine (Compound 8) exhibits grey matter to white matter (GM/WM) signal ratio of approximately 17.3±1.7.

The autoradiography signal of 3-(3-[18F]-fluoroazetidin-1-yl)-8-methylbenzo[4,5]imidazo[1,2-a]pyridine (Compound 8) on normal brain sections is weak and even, showing little difference between grey matter and white matter, indicative of low non-specific binding. From experiments according to Assay Example 5 the selectivity ratio of 3-(3-[18F]-fluoroazetidin-1-yl)-8-methylbenzo[4,5]imidazo[1,2-a]pyridine (Compound 8) binding to native tau aggregates, as compared to binding native β-amyloid aggregates in the grey matter region of human AD brains, is observed to be approximately 27 fold.

Autoradiography selectivity results with 3-(3-[18F]-fluoroazetidin-1-yl)-8-methylbenzo[4,5]imidazo[1,2-a]pyridine (Compound 8) demonstrate surprisingly advantageous selectivity in these experiments, when considered in comparison with 3-(4-(2-[18F]-fluoroethyl)piperidin-1-yl)-8-methoxybenzo[4,5]imidazo[1,2-a]pyridine (also known as T821 and shown below), and 3-(4-[18F]-fluoropiperidin-1-yl)-8-methoxybenzo[4,5]imidazol[1,2-a]pyridine (also known as T798 and shown below), which are recited as tau PET imaging agents in US2011/0182812.

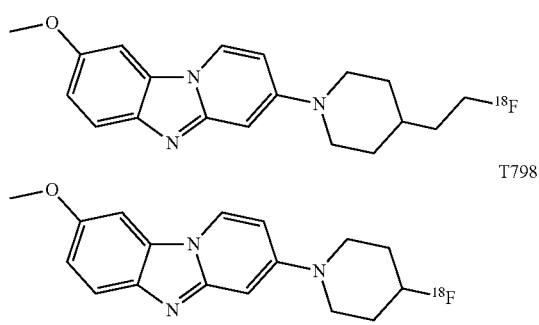

Figure 5:
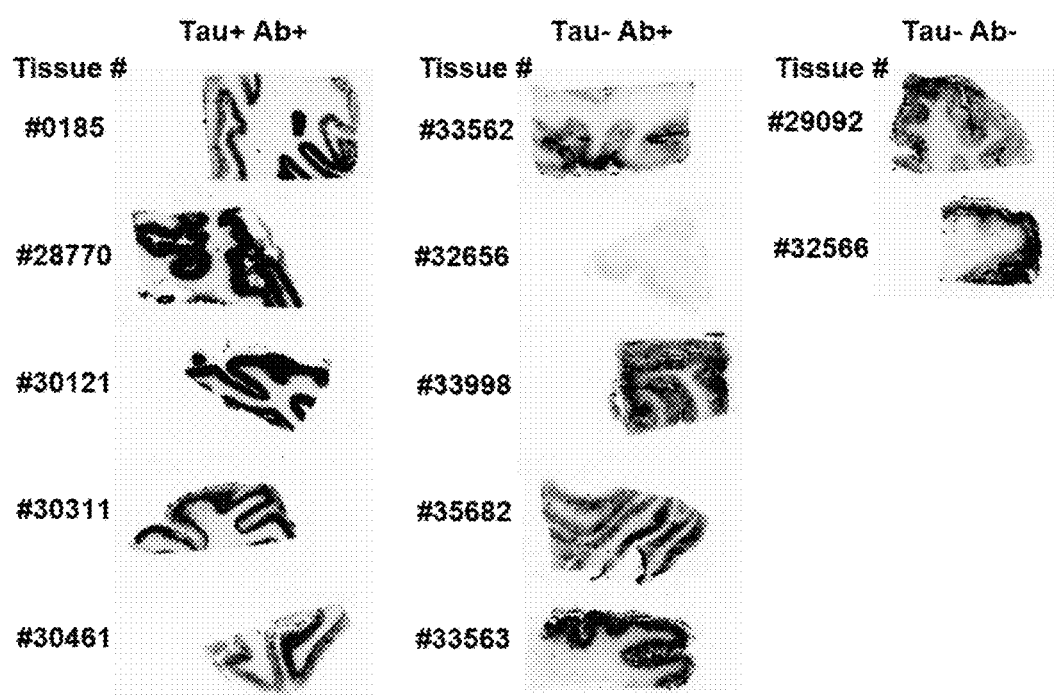
FIG. 5: 3-(4-(2-[18F]-Fluoroethyl)piperidin-1-yl)-8-methoxybenzo[4.5]imidazo[1,2-a]pyridine autoradiography on AD brain sections for selectivity determination See Assay Example 5 for an explanation of the experimental setup and analysis.

In experiments as outlined in Assay Example 5 and shown in FIG. 5, the compound 3-(4-(2-[18F]-fluoroethyl)piperidin-1-yl)-8-methoxybenzo[4,5]imidazo[1,2-a]pyridine (T821) exhibits a selectivity ratio for Tau:Aβ with of approximately 2.22±0.45, based on 5 Tau+Aβ+ brain specimens, and 2 Tau-Aβ+ brain specimens. As outlined in Assay Example 5 and shown in FIG. 5 the compound 3-(4-(2-[18F]-fluoroethyl)piperidin-1-yl)-8-methoxybenzo[4,5]imidazo[1,2-a]pyridine (T821) exhibits grey matter to white matter (GM/WM) signal ratio of approximately 11.7±1.2. Thus, the compound 3-(4-(2-[18F]-fluoroethyl)piperidin-1-yl)-8-methoxybenzo[4,5]imidazo[1,2-a]pyridine (T821) binds to tau, amyloid, and unidentified binding sites in normal human brain. This lack of selectivity represents a disadvantage for T821 for use in tau imaging.

Figure 6:
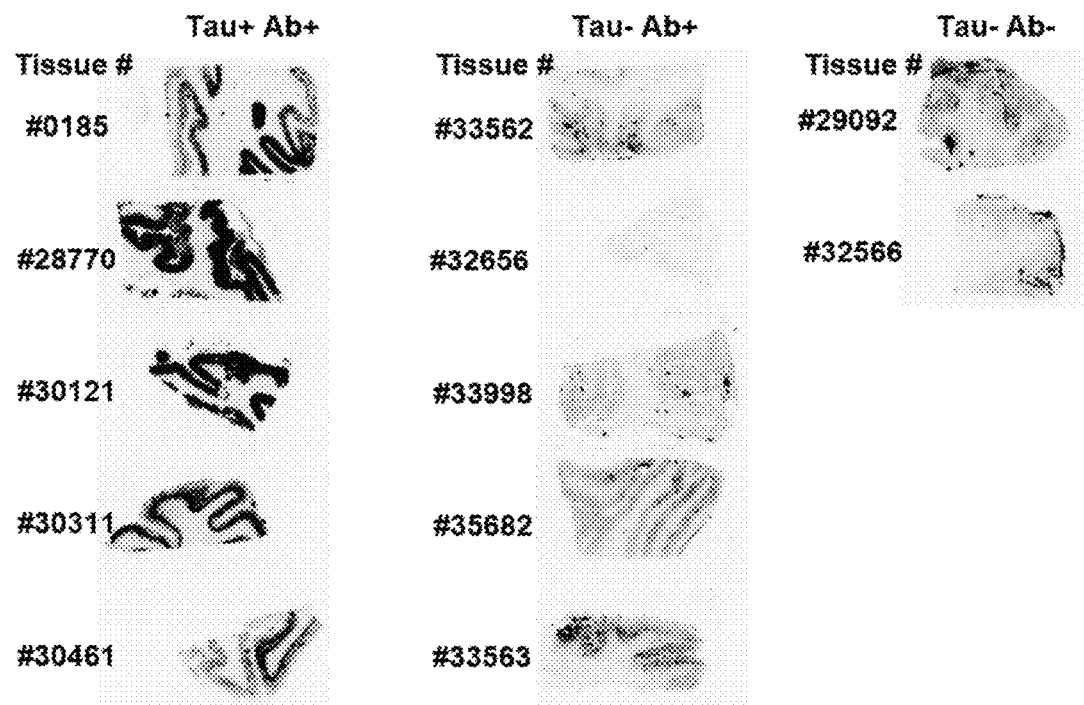
FIG. 6: 3-(4-[18F]-Fluoropiperidin-1-yl)-8-methoxybenzo[4,5]imidazo[1,2-a]pyridineautoradiography on AD brain sections for selectivity determination See Assay Example 5 for an explanation of the experimental setup and analysis.

In experiments as outlined in Assay Example 5 and shown in FIG. 6 the compound 3-(4-[18F]-fluoropiperidin-1-yl)-8-methoxybenzo[4,5]imidazo[1,2-a]pyridine (T798) exhibits a selectivity ratio for Tau:Aβ of approximately 8.4±1.7, based on 5 Tau+Aβ3+ brain specimens, and 2 Tau-Aβ+ brain specimens. As outlined in Assay Example 5 and shown in FIG. 6 the compound 3-(4-[18F]-fluoropiperidin-1-yl)-8-methoxybenzo[4,5]imidazo[1,2-a]pyridine (T798) exhibits grey matter to white matter (GM/WM) signal ratio of approximately 18.0±3.2, based on 5 Tau+Aβ+ brain specimens. Thus the compound 3-(4-[18F]-fluoropiperidin-1-yl)-8-methoxybenzo[4,5]imidazo[1,2-a]pyridine (T798) binds to tau, amyloid, and unidentified binding sites in normal human brain. This lack of selectivity represents a disadvantage for T798 for use in tau imaging.

Thus, T821 and T798 show, relative to Compound 8, poor selectivity, not only between tau and A-beta amyloid, but also between tau and unidentified binding sites observed in normal human brain tissue relatively devoid of tau and A-beta amyloid (See FIG. 4 for Compound 8, FIG. 5 for T821 and FIG. 6 for T798). 3-(4-(2-[18F]-Fluoroethyl)piperidin-1-yl)-8-methoxybenzo[4,5]imidazo[1,2-a]pyridine and 3-(4-[18F]-fluoropiperidin-1-yl)-8-methoxybenzo[4,5]imidazo[1,2-a]pyridine would not be useful PET tau imaging agents because of this lack of selectivity. In contrast, the selectivity of 3-(3-[18F]-fluoroazetidin-1-yl)-8-methylbenzo[4,5]imidazo[1,2-a]pyridine (Compound 8) binding to native tau aggregates, as compared with binding native β-amyloid aggregates in the grey matter region of human AD brains, is observed to be approximately 27 fold. This surprisingly selective binding property of Compound 8 would be particularly advantageous for tau imaging and could provide enhanced tau images, as compared with known agents, producing images with better clarity due to strong tau signals and decreased non-tau signals. Skilled artisans would know how to use radiopharmaceutical preparations of 3-(3-[18F]-fluoroazetidin-1-yl)-8-methylbenzo[4,5]imidazo[1,2-a]pyridine (Compound 8), either alone, or in comparison to existing beta amyloid imaging agents, to assess the accumulation and distribution of tau in clinical patient imaging.

Assay Example 6

Figure 7:
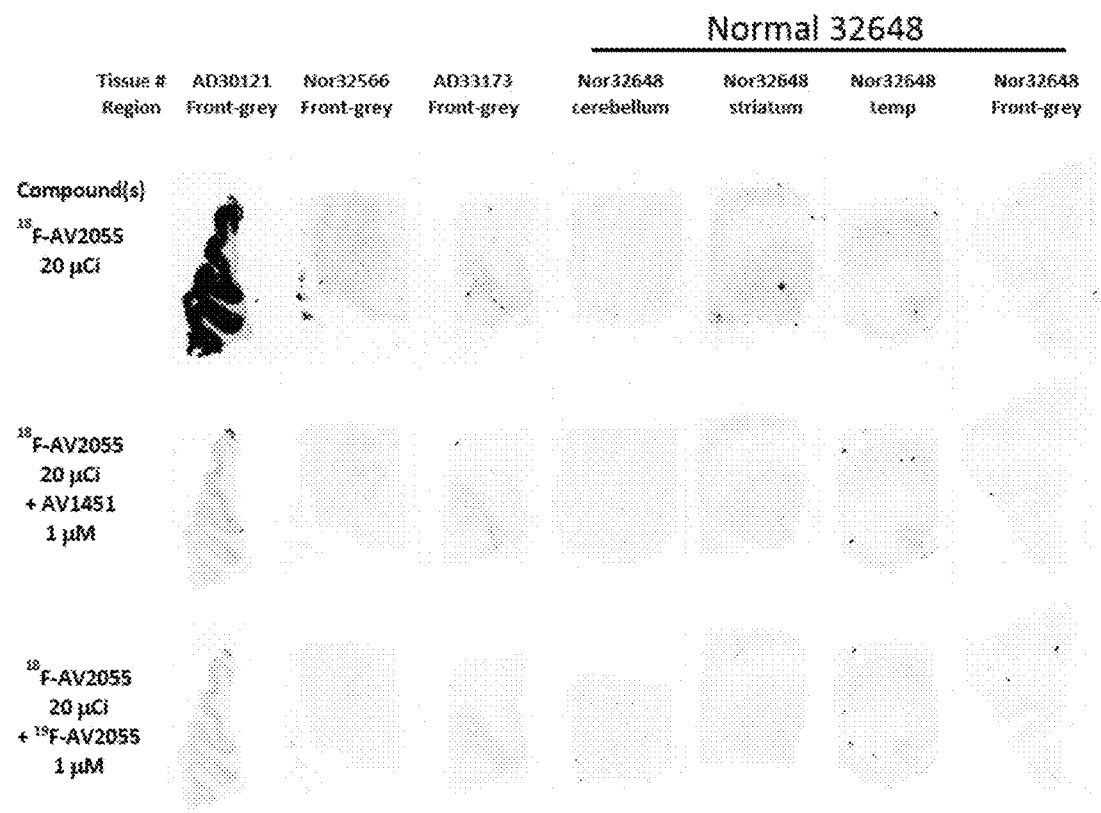
FIG. 7: 3-(3-[18F]-Fluoroazetidin-1-yl)-8-methylbenzo[4,5]imidazo[1,2-a]pyridine, Compound 8 autoradiography on normal versus AD brain sections. See Assay Example 6 for an explanation of the experimental setup and analysis.
Figure 8:
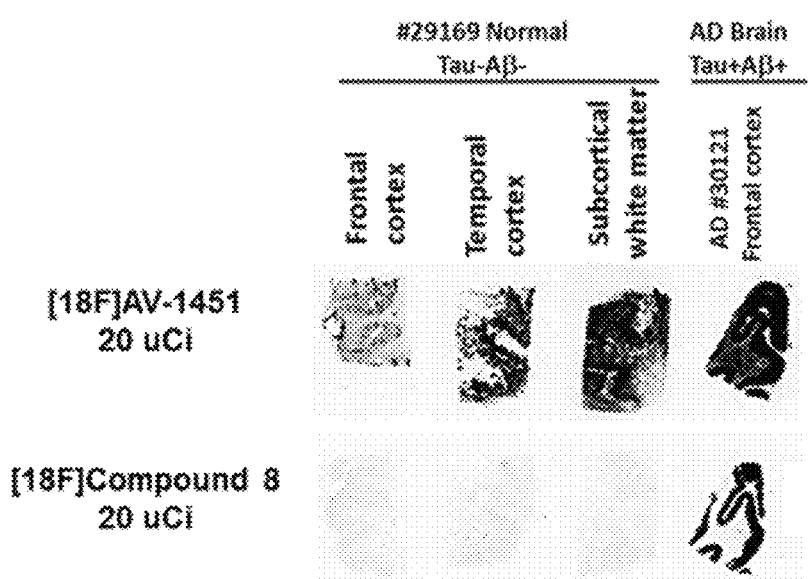
FIG. 8: 3-(3-[18F]-Fluoroazetidin-1-yl)-8-methylbenzo[4,5]imidazo[1,2-a]pyridine (Compound 8) and [18F]AV-1451 (also known as [18F]T807), autoradiography on normal versus AD brain sections using alcohol free washes. See Assay Example 6 for an explanation of the experimental setup and analysis.

Lack of Binding of 3-(3-[18F]-Fluoroazetidin-1-yl)-8-methylbenzo[4,5]imidazo[1,2-a]pyridine to Normal Human Brain Slices In order to show the absence of non-tau binding, autoradiography scans are obtained from 3-(3-[18F]-fluoroazetidin-1-yl)-8-methylbenzo[4,5]imidazo[1,2-a]pyridine on normal human brain tissue. The experimental procedure is the same as provided in Example 5 except that only 20 uCi of 18F-ligand is applied to the tissue slices and the washing conditions are less stringent. FIG. 7 shows that the radioactivity signal in normal tissue is considerably lower than in AD brain tissue when successive washing cycles (2 minutes in PBS, 2 minutes 10% ethanol/PBS, 2 minutes in 30% ethanol/PBS, 2 minutes in PBS) are used. The signal in the AD brain tissue (AD30121, frontal cortex) can be blocked by non-radiolabelled compound or with the known tau PET tracer T807 (also known as AV-1451), as would be expected for blocking tau-specific binding. The autoradiography is further carried out with no ethanol in the washing solutions. FIG. 8 shows that compared to [18F]T807 (also known as AV-1451), the tau tracer 3-(3-[18F]-fluoroazetidin-1-yl)-8-methylbenzo[4,5]imidazo[1,2-a]pyridine has much lower autoradiography signal in normal cortical or white matter tissue. This greatly reduced non-tau binding for Compound 8 on normal tissue represents a surprisingly advantageous improvement as compared to [18F]T807/AV-1451.

Assay Example 7

Mouse PET/CT Scan Obtained with 3-(3-[18F]-Fluoroazetidin-1-Yl)-8-methylbenzo[4,5]imidazo[1,2-a]pyridine Dynamic Micro-Positron Emission Tomography (mPET) images are obtained from CD-1 wild type mice using 3-(3-[18F]-fluoroazetidin-1-yl)-8-methylbenzo[4,5]imidazo[1,2-a]pyridine. Micro-Computed Tomography (mCT) of each subject is used as anatomical reference for image analysis. Biodistribution of the tracer in brain, muscle, bone, liver, and kidney is assessed by generating Time Activity Curves (TAC) using the fused mPET/mCT images. An INVEON multimodality scanner (Siemens, Germany) is used for mPET/mCT. All animal work is performed in accordance with the University of Sciences Institutional Animal Care & Use Committee-approved procedures.

Animals are anesthetized with 3% isoflurane/97% oxygen and are placed on the scanner bed. A short high-resolution CT scan is first performed for anatomical registration, followed by a 120-minute PET scan. During the PET scan a water heating system is placed underneath the bed to help maintain the body temperature. Within 3 minutes after the beginning of the PET acquisition, the [18F]-labeled compound 3-(3-[18F]-fluoroazetidin-1-yl)-8-methylbenzo[4,5]imidazo[1,2-a]pyridine is administered to the animals via tail vein injection (250 uCi in a total volume of 200 uL saline). A PET image is generated for each minute of the acquisition time. Uptake of the tracer is obtained by visually drawing regions of interest based on the fused PET/CT images, and the corresponding activity values are determined using the INVEON Research Workplace software (Siemens, Germany). All values are represented as percent injected dose per gram (% ID/g).

Time activity curves obtained from 3-(3-[18F]-fluoroazetidin-1-yl)-8-methylbenzo[4,5]imidazo[1,2-a]pyridine are compared with those obtained from the known tau PET tracer T807/AV-1451. 3-(3-[18F]-Fluoroazetidin-1-yl)-8-methylbenzo[4,5]imidazo[1,2-a]pyridine enters the brain with a higher % ID/g than [18F]AV-1451, is cleared quickly, and exhibits no significant uptake of radioactivity in bone tissue. These properties are advantageous for an improved brain imaging agent.

Assay Example 8

Mouse PET/CT Time Activity Curves of 3-(4-(2-[18F]-Fluoroethyl)piperidin-1-yl)-8-methoxybenzo[4,5]imidazo[1,2-a]pyridine (T821) and 3-(4-[18F]-Fluoropiperidin-1-yl)-8-methoxybenzo[4,5]imidazo[1,2-a]pyridine, (T798) versus 3-(3-[18F]-fluoroazetidin-1-yl)-8-methylbenzo[4,5]imidazol[1,2-a]pyridine (Compound 8)

Figure 9:
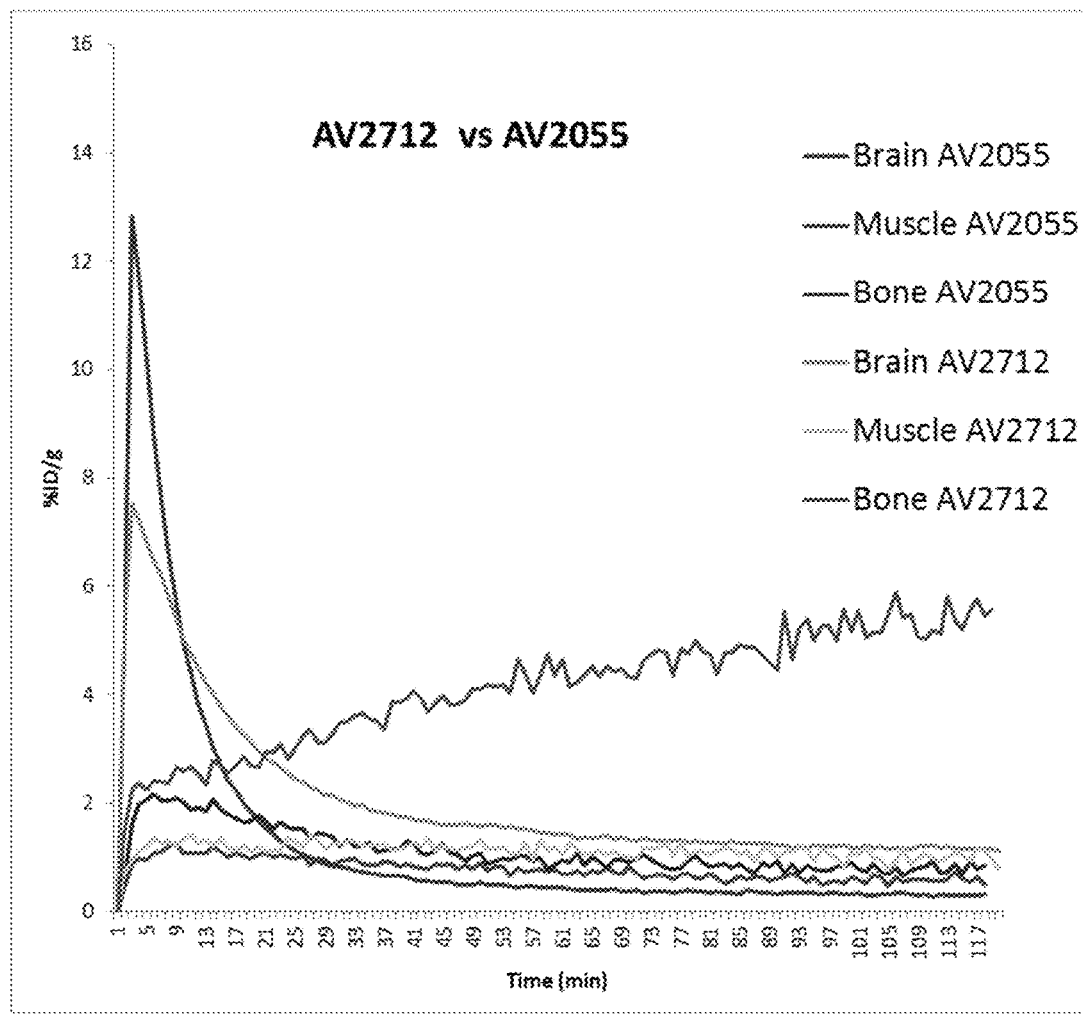
FIG. 9: Mouse PET/CT time activity curves of 3-(4-(2-[18F]-Fluoroethyl)piperidin-1-yl)-8-methoxybenzo[4,5]imidazo[1,2-a]pyridine (AKA T821) versus 3-(3-[18F]-Fluoroazetidin-1-yl)-8-methylbenzo[4,5]imidazo[1,2-a]pyridine (Compound 8).
Figure 10:
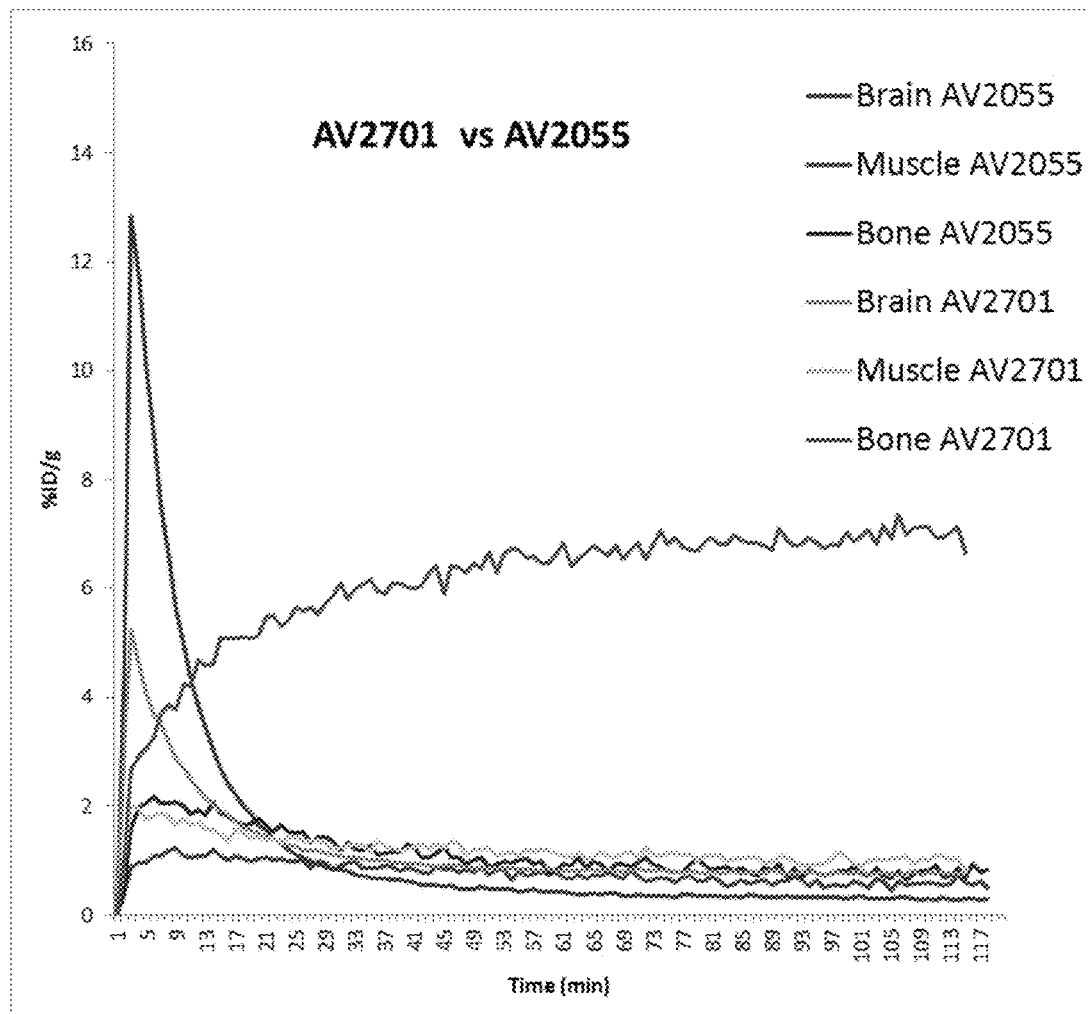
FIG. 10: Mouse PET/CT time activity curves of 3-(4-[18F]-Fluoropiperidin-1-yl)-8-methoxybenzo[4,5]imidazo[1,2-a]pyridine (AKA T798) versus 3-(3-[18F]-Fluoroazetidin-1-yl)-8-methylbenzo[4,5]imidazo[1,2-a]pyridine (Compound 8).

The mouse PET/CT time activity curves of 3-(4-(2-[18F]-fluoroethyl)piperidin-1-yl)-8-methoxybenzo[4,5]imidazo[1,2-a]pyridine (T821) (See FIG. 9) and of 3-(4-[18F]-fluoropiperidin-1-yl)-8-methoxybenzo[4,5]imidazo[1,2-a]pyridine (T798) (See FIG. 10) are obtained as described in Assay Example 7 (T821 and T798 are recited in US2011/0182812). FIGS. 9 and 10 illustrate that bone uptake of radioactivity increases with time for T821 and T798 indicating the likely release of radioactive fluoride ion that can label bone. Therefore, when imaging with T821 and/or T798, the undesirable non-tau PET signals from the skull bones could interfere with desired tau signals from the brain cortex. Thus, in addition to the lack of selectivity for T821 and T798, these compounds would further represent poor candidates for human brain tau PET tracers because of the interfering radioactivity signal from bone. In comparison, 3-(3-[18F]-fluoroazetidin-1-yl)-8-methylbenzo[4,5]imidazo[1,2-a]pyridine (Compound 8) causes negligible radioactivity signal in bone, and has significantly superior and surprising brain uptake compared to that of T821 and T798. 3-(3-[18F]-Fluoroazetidin-1-yl)-8-methylbenzo[4,5]imidazo[1,2-a]pyridine has surprisingly advantageous properties which are required for an improved tau PET imaging agent including a favorable tissue distribution, favorable PK properties, and a robust tau selectivity profile. The advantageous properties of Compound 8 are useful to provide enhanced tau PET imaging in humans. This combination of critical properties was not known and could not have been predicted from existing tau imaging compounds.

Assay Example 9

Biodistribution of 3-(3-[18F]-Fluoroazetidin-1-yl)-8-methylbenzo[4,5]imidazol[1,2-a]pyridine (Compound 8) in Normal Mice In order to determine the organ distribution, brain penetration and clearance in normal mice, 3-(3-[18F]-fluoroazetidin-1-yl)-8-methylbenzo[4,5]imidazo[1,2-a]pyridine is injected into normal mice followed by euthanasia and dissection at 2, 60, 120 and 180 minutes post injection. While under anesthesia, 0.2 mL of saline solution containing 20 μCi of 3-(3-[18F]-fluoroazetidin-1-yl)-8-methylbenzo[4,5]imidazo[1,2-a]pyridine is injected directly into the tail vein. Three mice are used per time point and sacrificed in a staggered manner. The following organs and fluids are collected: Blood, Spleen, Thyroid, Testes, Heart, Liver, Pancreas, Kidneys, Muscle, Skin, Stomach, Bone, Lungs, Brain, Intestines, Urogenital system. The organs are weighted and the radioactivity of each organ is counted in an Automatic Gamma Counter (Perkin Elmer). For the skin, bone, muscle and blood, a sample is counted and the total weight of the organ or fluid is estimated. A sample of the injected dose is counted as reference. The Percentage Injected Dose per Gram of tissue (% ID/g) is calculated for each organ.

A 9.53% dose/g level of 3-(3-[18F]-fluoroazetidin-1-yl)-8-methylbenzo[4,5]imidazo[1,2-a]pyridine is obtained in the brain at the 2 minute time point. Clearance from the brain to less than 10% of the peak occurred before the 30 min point and continued for 2 hours. Radioactivity distributed primarily to the liver, intestines, and kidneys in the first two minutes, and persists in the intestines over the two hour study period (Tables 4 and 5).

The levels of radioactivity in the liver and intestines together with a moderate presence in the urogenital system that include the bladder suggest that the compound and metabolites thereof clear through the hepatic and digestive systems. The absence of an increase in radioactivity in bone tissue shows that the compound and its metabolites do not undergo de-fluorination in the first two hours. Uptake by the muscle remains under 2% ID/g, which is favorable for projected human signal to noise ratios for PET imaging. These results indicate that Compound 8 demonstrates surprisingly advantageous tissue distribution, pharmacokinetics, and metabolic stability in vivo. These properties are particularly advantageous for an improved brain tau imaging agent.

TABLE 4

Biodistribution of 3-(3-[18F]-Fluoroazetidin-1-yl)-8-methylbenzo[4,5]imidazo[1,2-a]pyridine in normal mice per gram.

| Compound 8 | 2 minutes | | 30 minutes | | 60 minutes | | 120 minutes | |
|---|---|---|---|---|---|---|---|---|
| % dose/g | AVG | SD | AVG | SD | AVG | SD | AVG | SD |
| Blood | 2.52 | 0.84 | 1.14 | 0.32 | 0.87 | 0.46 | 0.50 | 0.03 |
| Lung | 26.50 | 9.25 | 5.11 | 0.84 | 4.01 | 1.42 | 2.02 | 0.53 |
| Heart | 4.79 | 0.65 | 0.76 | 0.12 | 0.49 | 0.20 | 0.27 | 0.02 |
| Liver | 7.32 | 2.61 | 2.76 | 0.73 | 3.10 | 0.88 | 1.35 | 0.14 |
| Spleen | 10.89 | 9.64 | 1.98 | 0.52 | 1.15 | 0.59 | 0.57 | 0.05 |
| Pancreas | 8.74 | 4.50 | 1.15 | 0.47 | 0.60 | 0.30 | 0.23 | 0.01 |
| Stomach | 4.14 | 4.58 | 3.10 | 2.14 | 2.78 | 0.74 | 0.81 | 0.63 |
| Intestine | 5.77 | 1.83 | 10.09 | 3.63 | 15.40 | 7.58 | 11.88 | 2.99 |
| Kidney | 39.08 | 19.02 | 5.98 | 2.01 | 4.32 | 4.96 | 1.19 | 0.48 |
| Testes | 1.78 | 0.71 | 1.56 | 0.58 | 0.88 | 0.57 | 0.31 | 0.04 |
| Fat | 1.09 | 0.61 | 0.63 | 0.26 | 0.27 | 0.17 | 0.11 | 0.03 |
| Tail | 14.93 | 8.01 | 2.77 | 1.83 | 2.10 | 1.77 | 0.84 | 0.20 |
| Urogenital | 4.33 | 2.10 | 22.15 | 11.37 | 13.95 | 13.18 | 30.39 | 40.67 |
| Brain | 9.53 | 3.41 | 0.39 | 0.13 | 0.26 | 0.07 | 0.23 | 0.08 |
| Thyroid | 6.01 | 0.80 | 0.81 | 0.10 | 0.68 | 0.09 | 0.60 | 0.19 |
| Muscle | 1.81 | 1.35 | 0.46 | 0.13 | 0.31 | 0.11 | 0.25 | 0.12 |
| Skin | 0.96 | 0.63 | 0.55 | 0.03 | 0.36 | 0.15 | 0.39 | 0.23 |
| Bone | 1.89 | 1.08 | 0.93 | 0.19 | 0.97 | 0.28 | 0.72 | 0.66 |
| Body leftover | 2.43 | 0.55 | 0.71 | 0.12 | 0.54 | 0.32 | 0.29 | 0.03 |

TABLE 5

Biodistribution of [18F] 3-(3-Fluoroazetidin-1-yl)-8-methylbenzo[4,5]imidazo[1,2-a]pyridine in normal mice per organ.

| Compound 8 | 2 minutes | | 30 minutes | | 60 minutes | | 120 minutes | |
|---|---|---|---|---|---|---|---|---|
| % dose/organ | AVG | SD | AVG | SD | AVG | SD | AVG | SD |
| Blood | 4.54 | 1.47 | 2.03 | 0.53 | 1.63 | 0.91 | 0.89 | 0.09 |
| Lung | 5.18 | 1.97 | 0.99 | 0.20 | 0.74 | 0.22 | 0.37 | 0.12 |
| Heart | 0.72 | 0.07 | 0.11 | 0.02 | 0.08 | 0.04 | 0.04 | 0.00 |
| Liver | 11.56 | 4.33 | 4.22 | 1.10 | 4.73 | 1.67 | 1.86 | 0.37 |
| Spleen | 1.00 | 0.88 | 0.19 | 0.04 | 0.12 | 0.05 | 0.05 | 0.00 |
| Pancreas | 1.31 | 0.56 | 0.15 | 0.03 | 0.13 | 0.07 | 0.03 | 0.00 |
| Stomach | 1.52 | 1.23 | 1.80 | 1.22 | 3.25 | 3.31 | 0.45 | 0.36 |
| Intestine | 15.39 | 4.25 | 28.28 | 9.63 | 32.10 | 31.56 | 32.80 | 10.45 |
| Kidney | 15.93 | 7.93 | 2.56 | 0.96 | 1.73 | 2.26 | 0.44 | 0.15 |
| Testes | 0.30 | 0.14 | 0.23 | 0.07 | 0.20 | 0.10 | 0.05 | 0.01 |
| Fat | 0.27 | 0.14 | 0.21 | 0.15 | 0.12 | 0.07 | 0.03 | 0.01 |
| Tail | 10.85 | 5.28 | 1.93 | 1.26 | 1.35 | 1.57 | 0.61 | 0.15 |
| Urogenital | 0.75 | 0.25 | 3.92 | 2.67 | 3.23 | 2.34 | 6.52 | 9.82 |
| Brain | 4.42 | 1.57 | 0.17 | 0.06 | 0.09 | 0.08 | 0.11 | 0.04 |
| Thyroid | 0.10 | 0.02 | 0.01 | 0.01 | 0.11 | 0.17 | 0.06 | 0.09 |
| Muscle | 19.01 | 14.26 | 4.68 | 1.16 | 3.30 | 1.29 | 2.51 | 1.16 |
| Skin | 3.74 | 2.48 | 2.10 | 0.06 | 1.44 | 0.64 | 1.46 | 0.78 |
| Bone | 6.87 | 4.00 | 3.31 | 0.57 | 3.62 | 1.17 | 2.50 | 2.31 |
| Body leftover | 38.48 | 9.59 | 10.62 | 1.69 | 8.64 | 5.23 | 4.42 | 0.21 |

Assay Example 10

3-(3-[18F]-Fluoroazetidin-1-yl)-8-methylbenzo[4,5]imidazo[1,2-a]pyridine (Compound 8) PET Imaging of Tau Protein in the Brain of Patients with Alzheimer's Disease Clinical evaluation of 3-(3-[18F]-Fluoroazetidin-1-yl)-8-methylbenzo[4,5]imidazo[1,2-a]pyridine (Compound 8) as a PET radioligand for imaging tau protein deposition in patients with AD or other neurodegenerative disorders is conducted in healthy volunteers. AD patients, or Chronic Traumatic Encephalopathy (CTE) subjects, by completion of one or more PET scans with Compound 8. Dynamic PET imaging is acquired on a Siemens ECAT EXACT HR+ over 150 minutes following Compound 8 or [18F]AV-1451 injection (0-60 and 90-150 minute imaging segments). Compound 8 or [18F]AV-1451 scans are acquired similarly in two imaging sessions. A brain MRI is also obtained. PET and MRI images are aligned and normalized, and ATLAS-based volumes of interest (VOI) are applied to the dynamic PET series. Compound 8 or [18F]AV-1451 are evaluated in terms of kinetic profile as well as target region to cerebellum standardized uptake value ratio (SUVr between 100-120 min) between healthy volunteers and AD or CTE subjects.

Distribution in healthy controls and AD subjects are similar within-subjects between Compound 8 and [18F]AV-1451. Compound 8 and [18F]AV-1451 show similar within-subject distribution for tau uptake across the brain for the AD subjects. Higher uptake is observed in cortical brain regions for AD subjects compared with healthy controls for both Compound 8 and [18F]AV-1451. Compound 8 shows higher peak brain uptake at ~8 SUV, compared with ~6 SUV for [18F]AV-1451. Compound 8 and [18F]AV-1451 display similar washout from the brain. Compound 8 metabolism is rapid with 5±3% (n=7) intact parent remaining at 60 min post injection.

Compound 8 SUVr curves rapidly equilibrate in healthy volunteer subjects in cortical regions, with values around 1.0-1.1, while in subcortical regions (putamen, thalamus), the uptake seems reduced compared to [18F]AV-1451. In AD subjects, similarly to [18F]AV-1451, Compound 8 SUVr curves do not reach equilibrium within the time frame of the study (150 min), while Compound 8 shows slightly higher SUVr values compared to [18F]AV-1451. Images with Compound 8 are clearer and interpreted as lower non-specific background signal. Compound 8 SUVr plots show good separation between healthy volunteer and AD subjects, where mean SUVr is ~1.1 for healthy volunteer subjects, and ~1.6 for AD subjects, averaged over all regions. Compound 8 shows a higher brain uptake compared to [18F]AV-1451 in both healthy volunteers and AD subjects, with max Compound 8 SUV ~50% higher than that of [18F]AV-1451.

Compound 8 distribution in a CTE subject shows small focal areas of elevated uptake. For the CTE subject, smaller volumes of interest are manually delineated in focal areas with high uptake (sub-regions of the inferior lateral parietal cortex, superior parietal cortex and posterior temporal cortex). Compound 8 SUVr curves in these sub-regions show elevated signal, reaching values of ~1.5, while other cortical regions remains close to 1.0, similar to healthy volunteer subjects.

Results such as those described in Assay Example 10, and other Assay Examples above, support the use of Compound 8 as an improved and advantageous PET imaging probe for detecting levels of aggregated tau protein in AD patients and/or other neurodegenerative disorders, such as CTE.

We claim:

1. A compound of the formula selected from the group consisting of:

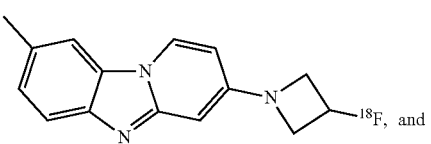

-continued

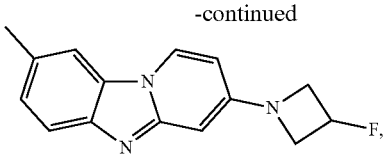

or pharmaceutically acceptable salt thereof.

2. A compound of the formula selected from the group consisting of:

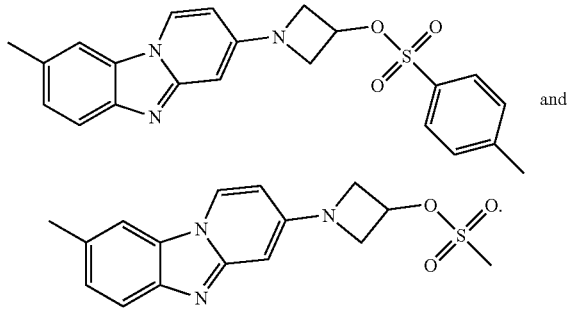

3. A process of making a compound of the formula:

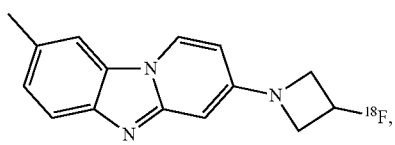

comprising reacting a compound of the formula selected from the group consisting of:

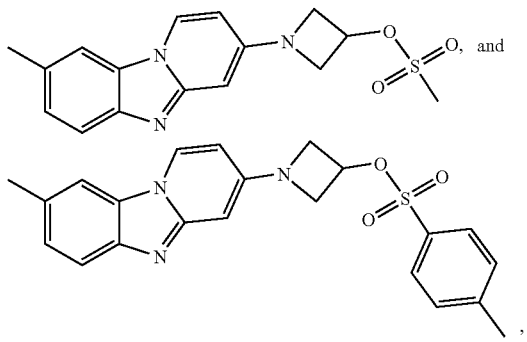

with a source of [$^{18}$F]fluoride.

4. A composition comprising a compound of the formula selected from the group consisting of

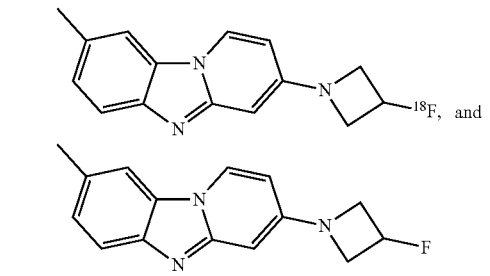

or a pharmaceutically acceptable salt thereof, and a pharmaceutically acceptable carrier or diluent.

5. A composition comprising

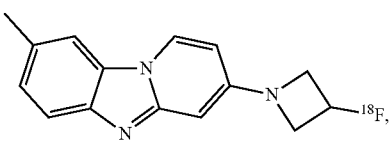

and 10% EtOH (v/v), 0.45% (w/v) sodium ascorbate in 0.9% sodium chloride.

6. A method of imaging aggregated tau comprising:
a. introducing into a mammal a detectable quantity of the compound:

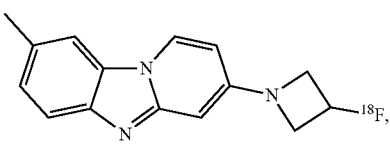

or a pharmaceutically acceptable salt thereof,
b. allowing sufficient time for said compound to become associated with tau; and
c. detecting said compound.

7. A method of claim 6 wherein the mammal is a human suspected of having Alzheimer's Disease.

8. A method of claim 6 wherein the mammal is a human suspected of having Chronic Traumatic Encephalopathy (CTE).

9. An intermediate for preparing a compound of claim 2 wherein the intermediate is 1-(8-methylbenzo[4,5]imidazo[1,2-a]pyridin-3-yl)azetidin-3-ol.

* * * * *